US007776853B2

(12) United States Patent
Hodson et al.

(10) Patent No.: US 7,776,853 B2
(45) Date of Patent: *Aug. 17, 2010

(54) 2-AMINO-BENZOXAZINONE DERIVATIVES FOR THE TREATMENT OF OBESITY

(75) Inventors: Harold Francis Hodson, Beckenham (GB); Robert Downham, Cambridge (GB); Timothy John Mitchell, Cambridge (GB); Beverley Jane Carr, Royston (GB); Christopher Robert Dunk, Ely (GB); Richard Michael John Palmer, Hayes (GB)

(73) Assignee: Norgine B.V., Amsterdam (NL)

( * ) Notice: Subject to any disclaimer, the term of this patent is extended or adjusted under 35 U.S.C. 154(b) by 1042 days.

This patent is subject to a terminal disclaimer.

(21) Appl. No.: 10/306,375

(22) Filed: Nov. 27, 2002

(65) Prior Publication Data

US 2003/0191123 A1 Oct. 9, 2003

Related U.S. Application Data

(60) Division of application No. 09/901,868, filed on Jul. 6, 2001, now Pat. No. 6,656,934, which is a continuation of application No. PCT/GB00/00031, filed on Jan. 6, 2000.

(30) Foreign Application Priority Data

Jan. 8, 1999 (GB) ................... 9900416.0

(51) Int. Cl.
*A61K 31/535* (2006.01)
(52) U.S. Cl. .................................. 514/230.5
(58) Field of Classification Search ................ 514/230.5
See application file for complete search history.

(56) References Cited

U.S. PATENT DOCUMENTS

| 3,450,700 | A |   | 6/1969  | Ulrich et al. ................. 260/244 |
|-----------|---|---|---------|----------------------------------------|
| 4,657,893 | A |   | 4/1987  | Krantz et al. ................. 514/18  |
| 4,665,070 | A |   | 5/1987  | Krantz et al. ............... 514/232   |
| 4,745,116 | A |   | 5/1988  | Krantz et al. ............ 514/230.5    |
| 5,776,756 | A | * | 7/1998  | Kimura et al. ............... 435/189   |
| 6,656,934 | B2| * | 12/2003 | Hodson et al. ........... 514/230.5     |

FOREIGN PATENT DOCUMENTS

| DE | 2315303    | 10/1974 |
|----|------------|---------|
| EP | 0147211    | 7/1985  |
| EP | 0206323    | 12/1986 |
| WO | WO96/07648 | 3/1996  |
| WO | WO96/37485 | 11/1996 |

OTHER PUBLICATIONS

Hays et al. "2-Amino-4H-3,1-benzoxazin-4-ones as Inhibitors of Clr Serine Protease" *J. Med. Chem.* 1998, 41, 1060-1067.

Krantz et al. "Design and Synthesis of 4H-3,1-Benzoxazin-4-ones as Potent Alternative Substrate Inhibitors of Human Leukocyte Elastase" *J. Med Chem.* 1990, 33, 464-479.
Krantz et al. "Design of Alternate Substrate Inhibitors of Serine Proteases. Synergistic Use of Alkyl Substitution to Impede Enzyme-Catalyzed Deacylation" *J. Med. Chem.* 1987, 30 (4), 589-590.
Krantz et al. "Design of Alternate Substrate Inhibitors of Serine Proteases: Tactics for Obstructing Deacylation Pathways" *Advances in Biosciences* 1987, 65, 213-220.
Neumann et al. "inhibition of Chymotrypsin and Pacreatic Elastase by 4H-3,1-Benzoxazin-4-ones" *J. Enzyme Inhibition*, 1991, 4, 227-232.
Gutschow et al. "Inhibition of Cathepsin G by 4H-3,1-Benzoxazin-4-ones"*Bioorg. Med. Chem.* 1997, 5, 1935-1942.
Jarvest et al. "Inhibition of HSV-1 Protease by Benzoxazinones" *Bioorg. Med. Chem.* 1996, 6, 2463-2466.
Torgerson, Jarl S., "Preventing diabetes in the obese: the XENDOS study and its context", *The British Journal of Diabetes and Vascular Disease*, 4(1): 22-27, 2004.
Textbook of Medicine, R.L. Souhami and J. Moxham, Longman Group UK Limited, 112-113, 435, 779, 1994.
Textbook of Medicine, R.L. Souhami and J. Moxham, Longman Group UK Limited, 561, 1994.
PCT/GB00/00031; copy of International Search Report mailed Dec. 12, 2000.

* cited by examiner

*Primary Examiner*—Alton N Pryor
(74) *Attorney, Agent, or Firm*—Choate, Hall & Stewart LLP; Charles E. Lyon; John P. Rearick

(57) ABSTRACT

The use of a compound comprising formula (I):

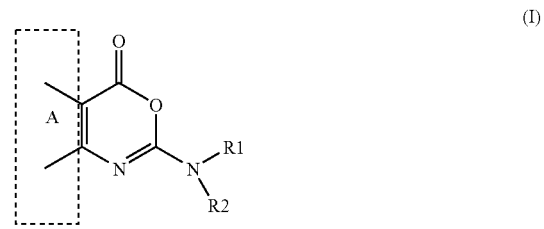

(I)

or a salt, ester, amide or prodrug thereof in the inhibition of an enzyme whose preferred mode of action is to catalyse the hydrolysis of an ester functionality, e.g. in the control and inhibition of unwanted enzymes in products and processes. The compounds are also useful in medicine e.g. in the treatment of obesity and related conditions. The invention also relates to novel compounds within formula (I), to processes for preparing them and pharmaceutical compositions containing them.

In formula (I) A is a 6-membered aromatic or heteroaromatic ring; and
$R^1$ is a branched or unbranched alkyl (optionally interrupted by one or more oxygen atoms), alkenyl, alkynyl, cycloalkyl, cycloalkenyl, aryl, arylalkyl, reduced arylalkyl, arylalkenyl, heteroaryl, heteroarylalkyl, heteroarylalkenyl, reduced aryl, reduced heteroaryl, reduced heteroarylalkyl or a substituted derivative of any of the foregoing groups.

36 Claims, No Drawings

2-AMINO-BENZOXAZINONE DERIVATIVES FOR THE TREATMENT OF OBESITY

PRIORITY INFORMATION

This application is a divisional application of U.S. Ser. No. 09/901,868, filed on Jul. 6, 2001 now U.S. Pat. No. 6,656,934. U.S. Ser. No. 09/901,868 is in turn a continuation of international application number PCT/GB00/00031, filed on Jan. 6, 2000, entitled "2-Amino-Benzoxazinone Derivatives for the Treatment of Obesity", which PCT application claims priority to GB 9900416.0, filed on—Jan. 8, 1999, and the entire contents of each of these is hereby incorporated by reference.

The present invention provides known and novel compounds, their use in the inhibition of an enzyme whose preferred mode of action is to catalyse the hydrolysis of an ester functionality (in vivo, as the enzyme naturally occurs), their use in medicine, and particularly in the prevention and/or treatment of obesity or an obesity-related disorder. Also provided are methods for the prevention and/or treatment of obesity or an obesity-related disorder and for promoting/aiding non-medical weight loss and the use of the compounds in the manufacture of a medicament for the aforementioned indications. In respect of novel compounds the invention also provides processes for their manufacture, compositions containing them, and methods for manufacturing such compositions.

In the last 20 years, there has been an increasing trend in obesity in the populations of the developed world. The increased incidence of obesity is due in part to the ready availability of food in numerous retail outlets and westernised diets that have high saturated fat and lower fibre contents such that the food is energy dense. The lifestyle of the populations of the developed world has also become more sedentary with the increased mechanisation of society and the steady reduction of manual labour intensive industries. There now exists an energy imbalance between the energy intake from calorie dense foods and the reduced energy expenditure required for a sedentary lifestyle. Some of the excess energy intake is stored as fat in the adipose tissue, the accumulation of which over a period of time results in obesity and can be a significant contributory factor to other diseases and disorders.

Obesity is now recognised by the medical profession as a metabolic disease. In the USA, it is estimated that 25% of the adult population is considered clinically obese (Body Mass Index >30). Obesity can be a debilitating condition which reduces the quality of life and increases the risk of related disorders such as diabetes, cardiovascular disease and hypertension. It has been estimated that $45 billion of US healthcare costs, or 8% per annum of total healthcare spend, is as a direct result of obesity. The traditional approaches to long term weight management such as diet and exercise have proved ineffective alone to control the spread of obesity. Today, more than ever, there is considerable interest in developing safe, effective drugs for the treatment of obesity.

Pharmacological approaches to the treatment of obesity have focused on either developing drugs that increase energy expenditure or drugs that reduce energy intake. One approach to the reduction of energy intake is to reduce the body's ability to digest and absorb food, in particular fat. The key enzymes involved in the digestion of fat are hydrolytic enzymes. The most significant of the fat degrading enzymes are lipases, primarily, but not exclusively pancreatic lipase that is secreted by the pancreas into the gut lumen. The lipase inhibitor lipstatin has formed the basis of the anti-obesity drug, orlistat. Orlistat is the subject of published European Patent Application No. EP129748, which relates to compounds of formula:

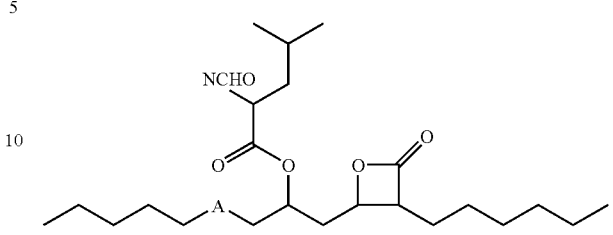

where A is —$(CH_2)_5$— or:

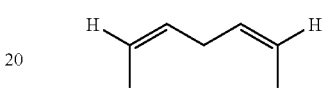

and their use in inhibiting pancreatic lipase and treating hyperlipaemia and obesity. Orlistat has as its major active moiety a beta-lactone group that reacts to form an ester with the side chain hydroxyl group of serine 152 within the active site of pancreatic lipase. Even if orlistat provides an effective method for treating obesity, there remains a need to provide alternative drugs and methods for use in the control and treatment of obesity, obesity-related disorders and non-medical weight loss. Inhibitors of enzymes involved in the degradation of fat are provided here and shown to be effective in the prevention and/or treatment of obesity, obesity-related disease and/or cosmetic weight loss.

U.S. Pat. No. 4,657,893 (Syntex) describes a broad class of 2-amino-4H-3,1-benzoxazin-4-ones of the formula:

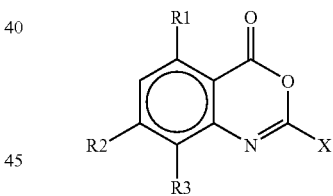

wherein $R^1$ is hydrogen or lower alkyl, $R^2$ and $R^3$ are each independently hydrogen, halo, lower alkyl, hydroxy, lower alkoxy, lower thioalkyl, —$NO_2$, —$N(R^1)_2$, —$NR^1COR^1$, —$NHCON(R^1)_2$ or $NHCOOR^1$; and X is inter alia —NHR where R is lower alkyl, lower alkenyl, lower alkynyl, optionally substituted lower cycloalkyl or optionally substituted phenyl lower alkyl. The compounds are said to be useful as serine protease inhibitors and to treat physiologic conditions and disease states known to involve serine proteases, or as contraceptives. The specification describes various conditions and diseases involving enzymatic pathways, including inflammation, arthritis, tumor cell metastasis, pulmonary emphysema, mucocutaneous lymph node syndrome, adult respiratory distress syndrome and pancreatitis. It is also suggested that the compounds may have antiparasitic, anticoagulant and/or antiviral activity. Similar compounds are also described by Krantz et al in *J. Med. Chem.* 1990 33:464-479.

2-Amino-4H-3,1-benzoxazin-4-ones as inhibitors of serine protease are also described by Hays et al in *J. Med.*

Chem. 1998 41:1060-1067. This paper describes inter alia 2-(substituted phenyl)amino benzoxazinones, where the phenyl substituents include halogen, methyl, SMe, and $OCF_3$, as well as certain 2-(heterocyclic)amino benzoxazinones. Some of these compounds are also described in U.S. Pat. No. 5,652, 237 (Warner Lambert).

German OLS 2315303 (Bayer AG) describes the preparation of compounds of the formula

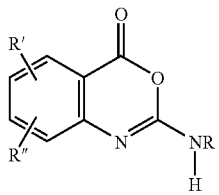

where R is an alkyl or aryl residue which may be substituted by nitro, halogen, alkyl, alkoxy or an aryl group, and R' and R" are each independently hydrogen, halogen, nitro, optionally substituted alkyl, cycloalkyl, aralkyl, aryl, alkoxy or aryloxy groups. The only values of R exemplified are nitrophenyl and mono- and di-chlorophenyl. The compounds are said to be useful as intermediates for pharmaceuticals and plant protection agents.

We have now found that a particular class of benzoxazinone compounds has activity as lipase inhibitors Accordingly, a first aspect of the invention provides a compound comprising formula (I)

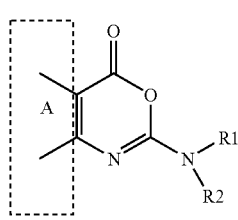

(I)

or a pharmaceutically acceptable salt, ester, amide or prodrug thereof; in the manufacture of a medicament for the treatment of conditions which require the inhibition of an enzyme whose preferred mode of action is to catalyse the hydrolysis of an ester functionality; wherein in formula (I):

A is a 6 membered aromatic or hetero-aromatic ring;

$R^1$ is a branched or unbranched alkyl (optionally interrupted by one or more oxygen atoms), alkenyl, alkynyl, cycloalkyl, cycloalkenyl, aryl, arylalkyl, reduced arylalkyl, arylalkenyl, heteroaryl, heteroarylalkyl, heteroarylalkenyl, reduced aryl, reduced heteroaryl, reduced heteroarylalkyl or a substituted derivative thereof wherein the substituents are one or more independently chosen from the group consisting of halogen, alkyl, halosubstituted alkyl, aryl, arylalkyl, heteroaryl, reduced heteroaryl, reduced heteroarylalkyl, arylalkoxy, cyano, nitro, $-C(O)R^4$, $-CO_2R^4$, $-SOR^4$, $-SO_2R^4$, $-NR^6R^7$, $-OR^6$, $-SR^6$, $-C(O)CX^1X^2NR^6R^7$, $-C(O)NR^4R^5$, $-C(O)N(OR^5)R^6$, $-NR^6C(O)R^4$, $-CR^6(NH_2)CO_2R^6$, $-NHCX^1X^2CO_2R^6$, $-N(OH)C(O)NR^6R^7$, $-N(OH)C(O)R^4$, $-NHC(O)NR^6R^7$, $-C(O)NHNR^6R^7$, $-C(O)N(OR^5)R^6$, or a lipid or steroid (natural or synthetic), with the proviso that any hetero atom substituent in $R^1$ and/or $R^2$ must be separated from the exocyclic nitrogen atom by at least two carbon atoms (preferably saturated); and $R^2$ is hydrogen or is a group as defined above for $R^1$; and where:

$R^4$ is hydrogen, alkyl, alkenyl, alkynyl, cycloalkyl, cycloalkenyl, aryl, arylalkyl, heteroaryl, heteroarylalkyl, reduced heteroaryl, reduced heteroarylalkyl, $-OR^6$, $-NHCX^1X^2CO_2R^6$ or $-NR^6R^7$;

$R^5$ is hydrogen, alkyl, alkenyl, alkynyl, cycloalkyl, cycloalkenyl, aryl, arylalkyl, heteroaryl, heteroarylalkyl, reduced heteroaryl or reduced heteroarylalkyl;

$R^6$ and $R^7$ are independently selected from hydrogen, alkyl, alkenyl, alkynyl, cycloalkyl, cycloalkenyl, aryl, arylalkyl, heteroaryl, reduced heteroaryl, heteroarylalkyl, reduced heteroarylalkyl or $-(CH_2)n(OR^5)m$ wherein n is 1 to 12, preferably 2 to 10, wherein m is 1-3 and $R^5$ is most preferably $C_{2-10}$ alkyl; and $X^1$ and $X^2$ are independently hydrogen, alkyl, alkenyl, alkynyl, cycloalkyl, cycloalkenyl, aryl, heteroaryl, arylalkyl, heteroarylalkyl, reduced heteroaryl or reduced heteroarylalkyl.

In compounds of formula (I) any alkyl, alkenyl and alkynyl groups and moieties may be straight chain (unbranched) or branched chain. Straight chain alkyl, alkenyl and alkynyl groups or moieties may contain from 1 to 30 carbon atoms, eg. 1 to 25 carbon atoms, preferably 1 to 20 carbon atoms. Branched chain alkyl, alkenyl and alkynyl groups or moieties may contain from 1 to 50 carbon atoms, preferably 1 to 30 carbon atoms.

Preferred values for $R^1$, $R^4$, $R^5$, $R^6$, $R^7$, $X^1$ and $X^2$ are as defined below for formulae (II) and (IIa). In particular, preferred values for $R^4$, $R^5$ and $R^6$ are as defined for $R^{13}$ and preferred values of $R^7$ are as defined for $R^{14}$ hereinbelow.

In this text, 'reduced', in the context of 'reduced heteroaryl' and the like means fully or partially saturated.

Aryl groups include for example optionally substituted unsaturated monocyclic or bicyclic rings of up to 12 carbon atoms, such as phenyl and naphthyl, and partially saturated bicyclic rings such as tetrahydro-naphthyl. Examples of substituents which may be present on an aryl group include one or more of halogen, amino, nitro, alkyl, haloalkyl, alkoxy, phenoxy and phenoxy substituted by one or more of halo, alkyl or alkoxy.

A heteroaryl group or moiety may be for example an optionally substituted 5- or 6-membered heterocyclic aromatic ring which may contain from 1 to 4 heteroatoms selected from O, N and S. The heterocyclic ring may optionally be fused to a phenyl ring. Examples of heteroaryl groups thus include furyl, thienyl, pyrrolyl, oxazolyl, oxazinyl, thiazolyl, imidazolyl, oxadiazolyl, thiadiazolyl, pyridyl, triazolyl, triazinyl, pyridazyl, pyrimidinyl, pyrazolyl, indolyl, indazolyl, benzofuranyl, benzothienyl, benzimidazolyl, benzoxazolyl, benzoxazinyl, quinoxalinyl, quinolinyl, quinazolinyl, cinnolinyl, benzothiazolyl, pyridopyrrolyl. Suitable substituents include one or more of halogen, oxo, amino, nitro, alkyl, haloalkyl, alkoxy, phenoxy and phenoxy substituted by one or more of halo, haloalkyl, alkyl or alkoxy.

A reduced heteroaryl group or moiety may be for example a fully or partially saturated derivative of the aforementioned heteroaryl groups. Examples of reduced heteroaryl groups thus include pyrrolidinyl, tetrahydrofuryl, tetrahydrothienyl and piperidinyl.

The compounds of the first aspect of the invention are useful inhibitors of enzymes involved in the degradation of fats. Preferably therefore the first aspect of the invention provides the use of a compound of formula (I) as defined hereinabove, or a pharmaceutically acceptable salt, ester, amide or prodrug thereof, in the manufacture of a medicament for the control or treatment of obesity, or obesity-related disorders or for promoting non-medical weight loss.

Preferably, a compound for use according to the first aspect of the invention is a compound of formula (II)

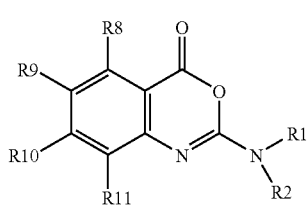

or a pharmaceutically acceptable salt, ester, amide or prodrug thereof;

wherein:

$R^1$, $R^4$, $R^5$, $R^6$, $R^7$, $X^1$ and $X^2$ are as defined above for formula I;

$R^2$ is hydrogen or is a group as defined above for $R^1$; and $R^8$, $R^9$, $R^{10}$, $R^{11}$ are each independently hydrogen, halo, hydroxy, amino, nitro, cyano, or a group $R^1$, as defined above;

or a group $R^{12}Q$ where Q is O, CO, CONH, NHCO, S, SO, $SO_2$, or $SO_2NH_2$ and $R^{12}$ is hydrogen or a group $R^1$ as defined above;

or a group $R^1R^2N$ where $R^1$ and $R^2$ are as defined above, with the proviso that any hetero atom substituent in $R^1$ and/or $R^2$ must be separated from the aromatic hetero atom substituent by at least two carbon atoms (preferably saturated).

In the compounds of formula (II):

$R^1$ preferably represents phenyl substituted by a group selected from $OR^{13}$, —$COR^{13}$, $CO_2R^{13}$, $SOR^{13}$, $SO_2R^{13}$, $CONR^{13}R^{14}$, $NR^{14}C(O)NR^{13}$, $C_{1-10}$alkyl, $C_{1-10}$alkoxy, halo$C_{1-10}$alkyl, aryl, aryl $C_{1-10}$alkyl, heteroaryl or heteroaryl $C_{1-10}$alkyl; wherein $R^{13}$ and $R^{14}$ each independently represents hydrogen, $C_{1-10}$alkyl, $C_{2-10}$alkenyl, $C_{2-10}$alkynyl, $C_{3-6}$cycloalkyl, $C_{3-6}$cycloalkenyl, aryl, aryl$C_{1-10}$alkyl, heteroaryl, heteroaryl$C_{1-10}$alkyl, reduced heteroaryl or reduced heteroaryl$C_{1-10}$alkyl.

More preferably $R^1$ represents phenyl substituted by $OR^{13}$ or $COR^{13}$ wherein $R^{13}$ is preferably aryl, most preferably phenyl; phenyl substituted by —$CO_2R^{13}$ wherein $R^{13}$ represents $C_{1-10}$alkyl, preferably $C_{1-6}$alkyl; or phenyl substituted by $C_{6-10}$alkyl.

$R^2$ preferably represents hydrogen or $C_{1-10}$alkyl;

$R^8$, $R^9$, $R^{10}$ and $R^{11}$ preferably each independently represents hydrogen, halo, hydroxy, amino, nitro, cyano, thiol, $C_{1-10}$alkyl, $C_{1-10}$alkoxy, $C_{1-10}$cycloalkyl, $C_{1-10}$cycloalkoxy, $C(O)R^{15}$, $C(O)NR^{15}R^{16}$, $S(O)R^{15}$ or halo $C_{1-10}$alkyl;

where $R^{15}$ and $R^{16}$ each independently represent hydrogen or $C_{1-10}$alkyl.

$R^8$ is hydrogen or halogen e.g. fluorine; most preferably hydrogen;

$R^9$ is preferably hydrogen or lower branched or unbranched alkyl having 1 to 10 carbon atoms: cyclic alkyl having 3 to 6 carbon atoms, e.g. cyclopropyl; halo$C_{1-6}$alkyl, e.g. trifluoromethyl; or a halogen, e.g. chlorine or fluorine;

$R^{10}$ is preferably hydrogen, lower branched or unbranched alkyl having 1 to 10 carbon atoms e.g. ethyl, butyl or octyl: cyclic alkyl having 3 to 6 carbon atoms, e.g. cyclopropyl; halo$C_{1-6}$alkyl, e.g. trifluoromethyl or a halogen, e.g. chlorine or fluorine;

$R^{11}$ is preferably hydrogen, halogen, eg. fluorine; or branched or unbranched alkyl having 1 to 10 carbon atoms.

Preferably, in compounds of formula (II) at least one of $R^8$, $R^9$, $R^{10}$ and $R^{11}$ represents a substituent other than hydrogen. Thus, for example, $R^8$ may represent a hydrogen atom and $R^9$, $R^{10}$ and $R^{11}$ are as defined above. In a preferred embodiment each of $R^8$ and $R^{11}$ represents a hydrogen atom, and one or both of $R^9$ and $R^{10}$ represents a substituent as defined above.

Preferably, a compound for use according to the first aspect of the invention comprises a compound of formula (II) or a pharmaceutically acceptable salt, ester, amide or prodrug thereof; wherein:

$R^1$ is aryl e.g. optionally substituted phenyl or 2-naphthyl, or an aryl alkyl group wherein the alkyl moiety has up to 25 e.g. up to 20 carbon atoms, or an aryl aryl group; wherein the aryl alkyl group or the aryl aryl group may be separated by a spacer where the spacer can be an ester, amide, O, $CH_2$, or a ketone and wherein any aryl group is preferably a phenyl, optionally substituted with alkyl, haloalkyl or halogen;

$R^2$ is hydrogen or is a group as defined above for $R^1$;

$R^8$ is hydrogen or fluorine;

$R^9$ is lower branched or unbranched alkyl having 1 to 10 carbon atoms; cyclic alkyl having 3 to 10 carbon atoms, e.g. cyclopropyl; haloalkyl, e.g. trifluoromethyl; or a halogen, e.g. chlorine or fluorine;

$R^{10}$ is lower branched or unbranched alkyl having 1 to 10 carbon atoms; e.g. ethyl, butyl or octyl, cyclic alkyl having 3 to 10 carbon atoms, e.g. cyclopropyl; haloalkyl, e.g. trifluoromethyl; or a halogen, e.g. chlorine or fluorine;

$R^{11}$ is hydrogen, lower branched or unbranched alkyl having 1 to 10 carbon atoms, or halogen, e.g. fluorine.

Most preferably, $R^1$ is unsubstituted phenyl or phenyl substituted by a group selected from $C_{1-8}$ alkyl, eg butyl, pentyl, hexyl or heptyl; halo-$C_{1-8}$ alkyl, eg $CF_3$; $OR^6$ where $R^6$ is phenyl or $COR^4$ where $R^4$ is phenyl or $C_{1-8}$ alkyl.

In a second aspect the present invention provides novel compounds of formula (IIa):

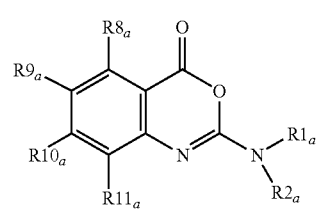

or a pharmaceutically acceptable salt, ester, amide or prodrug thereof;

wherein:

$R^{1a}$ represents (i) a $C_{10-30}$ branched or unbranched alkyl, $C_{2-30}$ alkenyl, $C_{2-30}$ alkynyl, cycloalkenyl, aryl-$C_{10-30}$ alkyl, aryl-$C_{10-30}$ alkenyl, heteroaryl, heteroaryl-$C_{1-30}$ alkyl, heteroaryl-$C_{2-30}$ alkenyl, reduced aryl, reduced heteroaryl, reduced heteroaryl-$C_{1-30}$ alkyl or a substituted derivative thereof wherein the substituents are one or more independently chosen from the group consisting of halogen, $C_{1-10}$ alkyl, halosubstituted $C_{1-10}$ alkyl, aryl, aryl-$C_{1-10}$ alkyl, heteroaryl, reduced heteroaryl, reduced heteroaryl-$C_{1-10}$ alkyl, aryl-$C_{1-10}$ alkoxy, cyano, nitro, —C(O)R$^{13}$, —CO$_2$R$^{13}$, —SOR$^{13}$, —SO$_2$R$^{13}$, —NR$^{13}$R$^{14}$, —OR$^{13}$, —SR$^{13}$, —C(O)NR$^{13}$R$^{14}$, and —NR$^{14}$C(O)R$^{13}$, with the proviso that any hetero atom substituent in R$^1$ must be separated from the exocyclic nitrogen atom by at least two carbon atoms (preferably saturated); or (ii) aryl substituted by one or more independently chosen from the group consisting of halosubstituted $C_{1-10}$ alkyl, aryl, aryl-$C_{1-10}$ alkyl, heteroaryl, reduced heteroaryl, reduced heteroaryl-$C_{1-10}$ alkyl, aryl-$C_{1-10}$ alkoxy, cyano, —C(O)R$^{13}$, —CO$_2$R$^{13}$, —SOR$^{13}$, —SO$_2$R$^{13}$, —NR$^{13}$R$^{14}$, —OR$^{13}$ (providing that in this instance R$^{13}$ does not represent aryl or alkyl), —SR$^{13}$, —C(O)NR$^{13}$R$^{14}$, and —NR$^{14}$C(O)R$^{13}$ wherein:
R$^{13}$ and R$^{14}$ each independently represents hydrogen, $C_{1-10}$alkyl, $C_{2-10}$alkenyl, $C_{2-10}$alkynyl, $C_{3-6}$cycloalkyl, $C_{3-6}$cycloalkenyl, aryl, arylC$_{1-10}$alkyl, heteroaryl, heteroarylC$_{1-10}$alkyl, reduced heteroaryl or reduced heteroarylC$_{1-10}$alkyl;

R$^{2a}$ is hydrogen or is a group as defined above for R$^1$; and R$^{8a}$, R$^{9a}$, R$^{10a}$, R$^{11a}$ are as defined above for formula (II).

provided that:
when R$^1$ represents a heteroaryl group it is not thiadiazolyl, triazolyl or thiazolyl and when R$^1$ represents a reduced heteroaryl group it is not thiazolidinyl.

In the compounds of formula (IIa):
R$^{1a}$ preferably represents phenyl substituted by a group selected from OR$^{13}$ (providing in this instance R$^{13}$ does not represent alkyl or aryl), —COR$^{13}$, CO$_2$R$^{13}$, SOR$^{13}$, SO$_2$R$^{13}$, CONR$^{13}$R$^{14}$, NR$^{14}$C(O)NR$^{13}$, haloC$_{1-10}$alkyl, aryl, aryl C$_{1-10}$alkyl, heteroaryl or heteroaryl C$_{1-10}$alkyl.

More preferably R$^{1a}$ represents phenyl substituted by COR$^{13}$ wherein R$^{13}$ is preferably aryl, most preferably phenyl; or phenyl substituted by —CO$_2$R$^{13}$ wherein R$^{13}$ represents $C_{1-10}$alkyl, preferably $C_{1-6}$alkyl.

R$^{2a}$ preferably represents hydrogen or $C_{1-10}$alkyl;
R$^{8a}$, R$^{9a}$, R$^{10a}$ and R$^{11a}$ preferably each independently represents hydrogen, halo, hydroxy, amino, nitro, cyano, thiol, $C_{1-10}$alkyl, $C_{1-10}$alkoxy, $C_{1-10}$cycloalkyl, $C_{1-10}$cycloalkoxy, C(O)R$^{15}$, C(O)NR$^{15}$R$^{16}$, S(O)R$^{4a}$ or halo $C_{1-10}$alkyl;
where R$^{15}$ and R$^{16}$ each independently represent hydrogen or $C_{1-10}$alkyl.

R$^{8a}$ is hydrogen or halogen e.g. fluorine; most preferably hydrogen;
R$^{9a}$ is preferably hydrogen or lower branched or unbranched alkyl having 1 to 10 carbon atoms; cyclic alkyl having 3 to 6 carbon atoms; e.g. cyclopropyl, haloC$_{1-6}$alkyl, e.g. trifluoromethyl or a halogen, e.g. chlorine or fluorine;
R$^{10a}$ is more preferably hydrogen, lower branched or unbranched alkyl having 1 to 10 carbon atoms e.g. ethyl, butyl or octyl; cyclic alkyl having 3 to 6 carbon atoms e.g. cyclopropyl, haloC$_{1-6}$alkyl e.g. trifluoromethyl or a halogen e.g. chlorine or fluorine;
R$^{11a}$ is preferably hydrogen, halogen, eg. fluorine; or branched or unbranched alkyl having 1 to 10 carbon atoms.

Preferably, in compounds of formula (IIa) at least one of R$^{8a}$, R$^{9a}$, R$^{10a}$ and R$^{11a}$ represents a substituent other than hydrogen. Thus, for example, R$^{8a}$ may represent a hydrogen atom and R$^{9a}$, R$^{10a}$ and R$^{11a}$ areas defined above. In a preferred embodiment each of R$^{8a}$ and R$^{11a}$ represents a hydrogen atom, and one or both of R$^{9a}$ and R$^{10a}$ represents a substituent as defined above. In a yet further embodiment the present invention provides compounds of formula

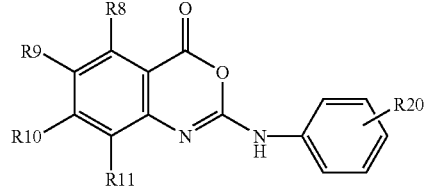
(IIb)

wherein
R$^8$-R$^{11}$ are as defined hereinbefore and
R$^{20}$ represents $C_{1-20}$alkyl, $C_{1-20}$alkoxy, or optionally substituted phenoxy.

Preferred substituents for phenoxy include one or more of halo, CF$_3$, lower alkyl and lower alkoxy groups.

When R$^{20}$ represents an alkyl or alkoxy group this preferably contains from 6-12 carbon atoms.

In this embodiment R$^{20}$ is most preferably phenoxy.

Preferred values of R$^8$-R$^{11}$ are as defined above.

Compounds of formula (IIb) represent a novel selection on the basis of their advantageous activity as lipase inhibitors.

Examples of pharmaceutically acceptable salts of the formula include those derived from organic acids such as methanesulphonic acid, benzenesulphonic acid and p-toluenesulphonic acid, mineral acids such as hydrochloric and sulphuric acid and the like, giving methanesulphonate, benzenesulphonate, p-toluenesulphonate, hydrochloride and sulphate, and the like, respectively or those derived from bases such as organic and inorganic bases. Examples of suitable inorganic bases for the formation of salts of compounds for this invention include the hydroxides, carbonates, and bicarbonates of ammonia, lithium, sodium, calcium, potassium, aluminium, magnesium, zinc and the like. Salts can also be formed with suitable organic bases. Such bases suitable for the formation of pharmaceutically acceptable base addition salts with compounds of the present invention include organic bases which are nontoxic and strong enough to form salts. Such organic bases are already well known in the art and may include amino acids such as arginine and lysine, mono-, di-, or trihydroxyalkylamines such as mono-, di-, and triethanolamine, choline, mono-, di-, and trialkylamines, such as methylamine, dimethylamine, and trimethylamine, guanidine; N-methylglucosamine; N-methylpiperazine; morpholine; ethylenediamine; N-benzylphenethylamine; tris(hydroxymethyl) aminomethane; and the like.

Salts may be prepared in a conventional manner using methods well known in the art. Acid addition salts of said basic compounds may be prepared by dissolving the free base compounds according to the first or second aspects of the invention in aqueous or aqueous alcohol solution or other suitable solvents containing the required acid. Where a compound of formula (I) contains an acidic function a base salt of said compound may be prepared by reacting said compound with a suitable base. The acid or base salt may separate directly or can be obtained by concentrating the solution eg. by evaporation. The compounds of this invention may also exist in solvated or hydrated forms.

The invention also extends to prodrugs of the aforementioned compounds. A prodrug is commonly described as an inactive or protected derivative of an active ingredient or a drug which is converted to the active ingredient or drug in the body.

Representative compounds according to the first and/or second aspects of the invention are those which include;

TABLE 1

| Reference Number | Structure | Compound Name |
|---|---|---|
| 1 | 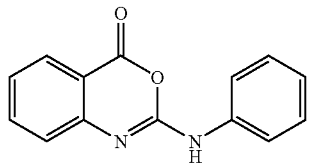 | 2-Phenylamino-4H-3,1-benzoxazin-4-one |
| 2 | 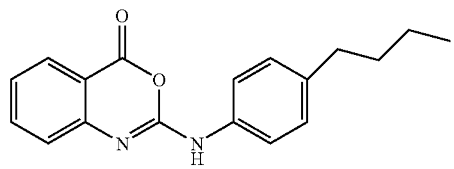 | 2-(4-Butylphenylamino)-4H-3,1-benzoxazin-4-one |
| 3 | 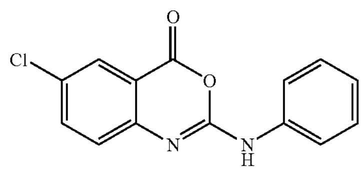 | 6-Chloro-2-phenylamino-4H-3,1-benzoxazin-4-one |
| 4 | 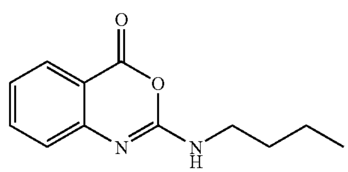 | 2-Butylamino-4H-3,1-benzoxazin-4-one |
| 5 | 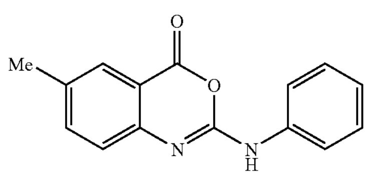 | 6-Methyl-2-phenylamino-4H-3,1-benzoxazin-4-one |
| 6 | 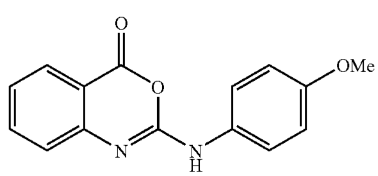 | 2-(4-Methoxyphenylamino)-4H-3,1-benzoxazin-4-one |
| 7 | 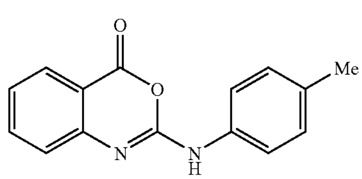 | 2-(4-Methylphenylamino)-4H-3,1-benzoxazin-4-one |
| 8 | 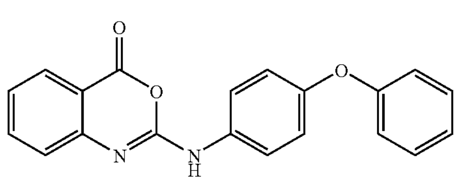 | 2-(4-Phenoxyphenylamino)-4H-3,1-benzoxazin-4-one |

TABLE 1-continued

| Reference Number | Structure | Compound Name |
| --- | --- | --- |
| 9 | 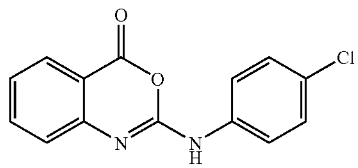 | 2-(4-Chlorophenylamino)-4H-3,1-benzoxazin-4-one |
| 10 | 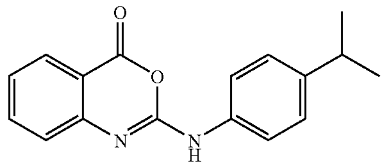 | 2-[4(1-Methylethyl)phenylamino]-4H-3,1-benzoxazin-4-one |
| 11 | 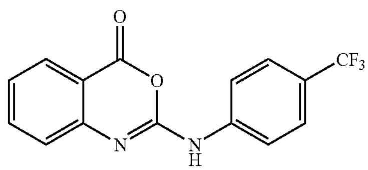 | 2-(4-Trifluoromethylphenylamino)-4H-3,1-benzoxazin-4-one |
| 12 | 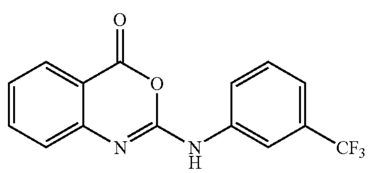 | 2-(3-Trifluoromethyl phenylamino)-4H-3,1-benzoxazin-4-one |
| 13 | 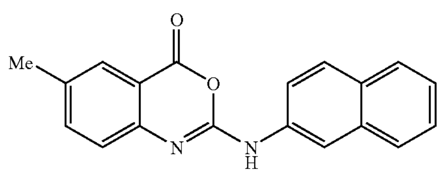 | 6-Methyl-2-(naphth-2-ylamino)-4H-3,1-benzoxazin-4-one |
| 14 | 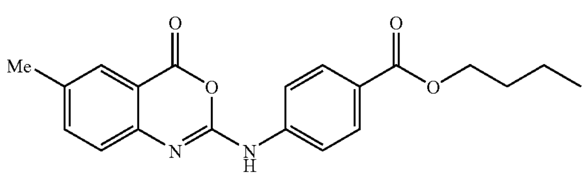 | 2-(4-Butoxycarbonyl phenylamino)-6-methyl-4H-3,1-benzoxazin-4-one |
| 15 | 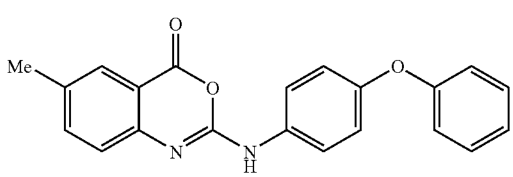 | 6-Methyl-2-(4-phenoxy phenylamino)-4H-3,1-benzoxazin-4-one |
| 16 | 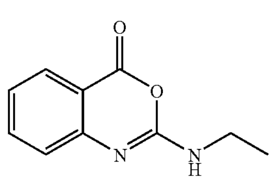 | 2-Ethylamino-4H-3,1-benzoxazin-4-one |

TABLE 1-continued

| Reference Number | Structure | Compound Name |
|---|---|---|
| 17 | 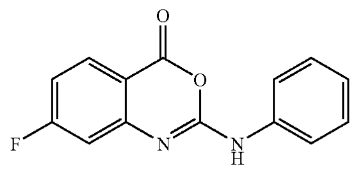 | 7-Fluoro-2-phenylamino-4H-3,1-benzoxazin-4-one |
| 18 | 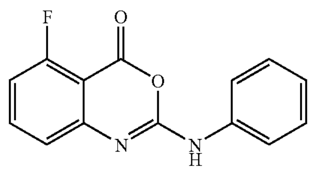 | 5-Fluoro-2-phenylamino-4H-3,1-benzoxazin-4-one |
| 19 | 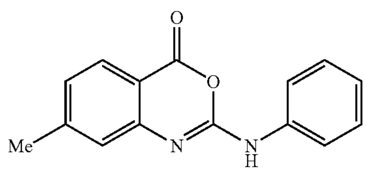 | 7-Methyl-2-phenylamino-4H-3,1-benzoxazin-4-one |
| 20 | 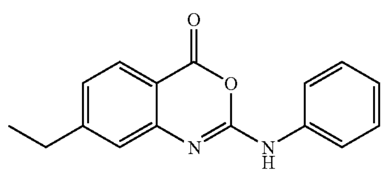 | 7-Ethyl-2-Phenylamino-4H-3,1-benzoxazin-4-one |
| 21 | 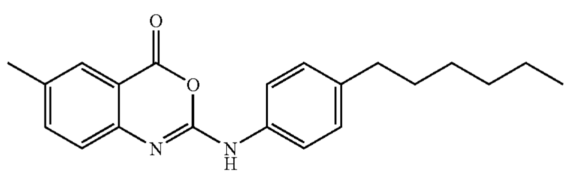 | 2-(4-Hexylphenylamino)-6-methyl-4H-3,1-benzoxazin-4-one |
| 22 | 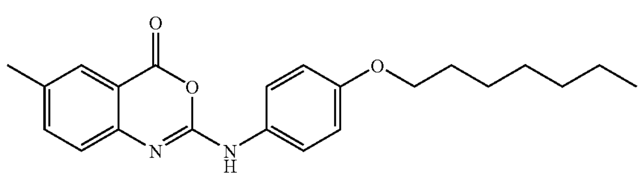 | 2-(4-Heptyloxyphenylamino)-6-methyl-4H-3,1-benzoxazin-4-one |
| 23 | 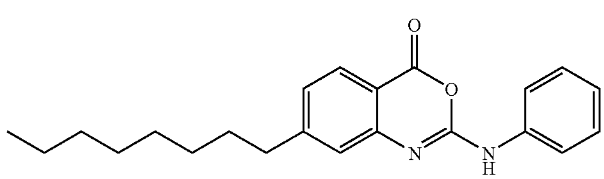 | 7-Octyl-2-phenylamino-4H-3,1-benzoxazin-4-one |
| 24 | 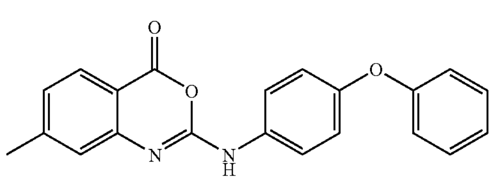 | 7-Methyl-2-(4-phenoxy phenylamino)-4H-3,1-benzoxazin-4-one |

TABLE 1-continued

| Reference Number | Structure | Compound Name |
|---|---|---|
| 25 | 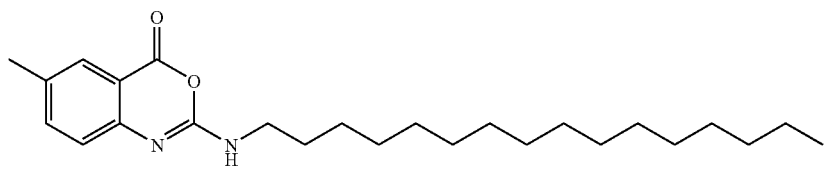 | 2-Hexadecylamino-6-methyl-4H-3,1-benzoxazin-4-one |
| 26 | 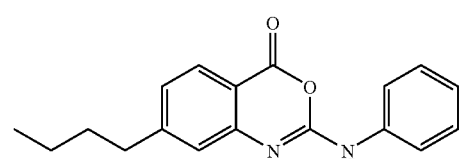 | 7-Butyl-2-phenylamino-4H-3,1-benzoxazin-4-one |
| 27 | 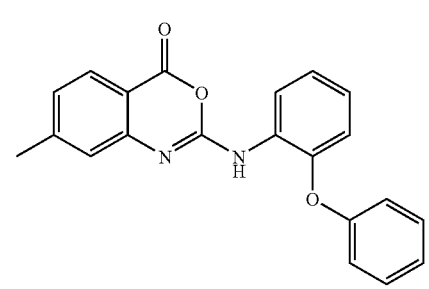 | 7-Methyl-2-(2-phenoxyphenylamino)-4H-3,1-benzoxazin-4-one |
| 28 | 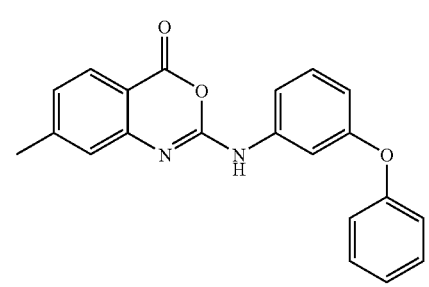 | 7-Methyl-2-(3-phenoxyphenylamino)-4H-3,1-benzoxazin-4-one |
| 29 | 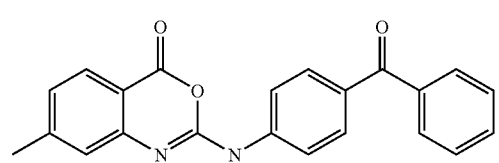 | 2-(4-Benzoylphenylamino)-7-methyl-4H-3,1-benzoxazin-4-one |
| 30 | 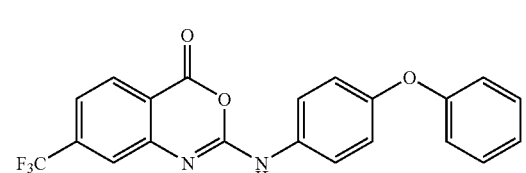 | 2-(4-Phenoxyphenylamino)-7-trifluoromethyl-4H-3,1-benzoxazin-4-one |
| 31 | 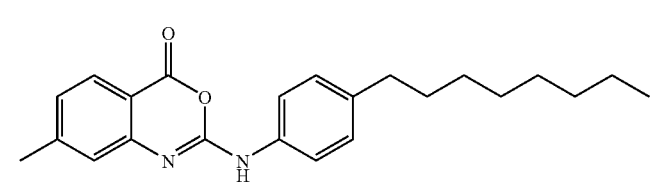 | 7-Methyl-2-(4-octylphenylamino)-4H-3,1-benzoxazin-4-one |

TABLE 1-continued

| Reference Number | Structure | Compound Name |
|---|---|---|
| 32 | 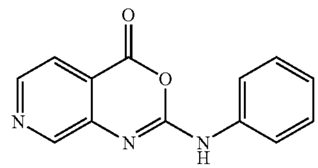 | 2-Phenylamino-4H-pyrido[3,4-d][1,3]oxazin-4-one |
| 33 | 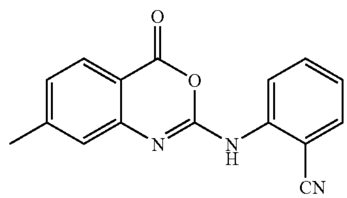 | 2-(2-Cyanophenylamino)-7-methyl-4H-3,1-benzoxazin-4-one |
| 34 | 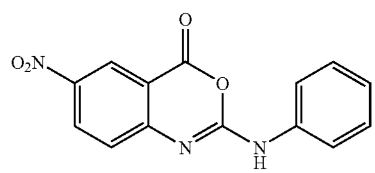 | 6-Nitro-2-phenylamino-4H-3,1-benzoxazin-4-one |
| 35 | 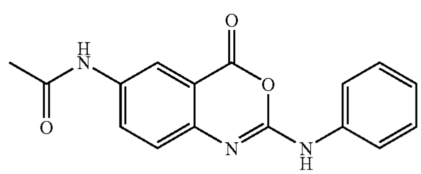 | 6-Acetamido-2-phenylamino-4H-3,1-benzoxazin-4-one |
| 36 | 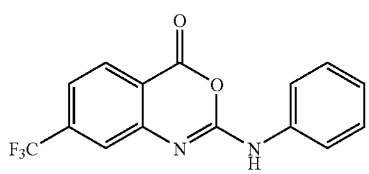 | 2-Phenylamino-7-trifluoromethyl-4H-3,1-benzoxazin-4-one |
| 37 | 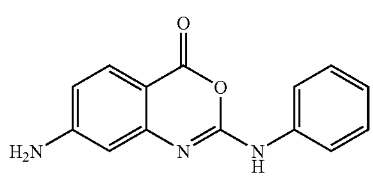 | 7-Amino-2-phenylamino-4H-3,1-benzoxazin-4-one |
| 38 | 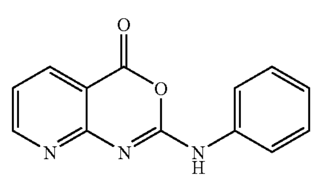 | 2-Phenylamino-4H-pyrido[2,3-d][1,3]oxazin-4-one |
| 39 | 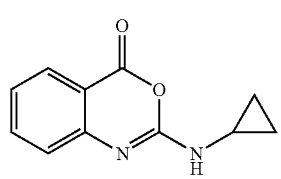 | 2-Cyclopropylamino-4H-3,1-benzoxazin-4-one |

TABLE 1-continued

| Reference Number | Structure | Compound Name |
|---|---|---|
| 40 | 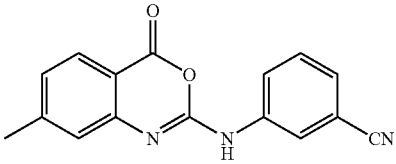 | 2-(3-Cyanophenylamino)-7-methyl-4H-3,1-benzoxazin-4-one |
| 41 | 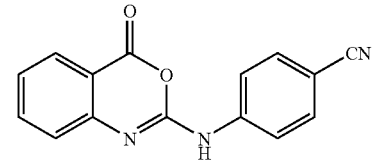 | 2-(4-Cyanophenylamino)-4H-3,1-benzoxazin-4-one |
| 42 | 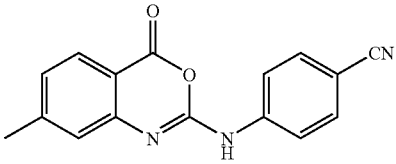 | 2-(4-Cyanophenylamino)-7-methyl-4H-3,1-benzoxazin-4-one |
| 43 | 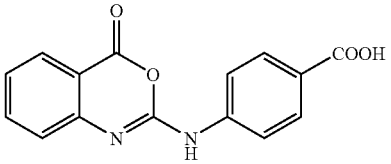 | 2-(4-Carboxyphenylamino)-4H-3,1-benzoxazin-4-one |
| 44 | 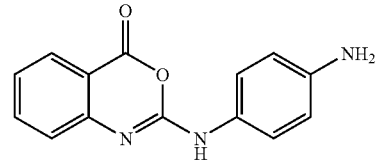 | 2-(4-Aminophenylamino)-4H-3,1-benzoxazin-4-one |
| 45 | 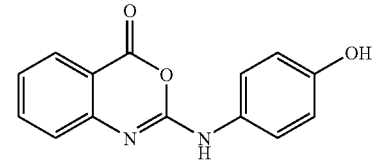 | 2-(4-Hydroxyphenylamino)-4H-3,1-benzoxazin-4-one |
| 46 | 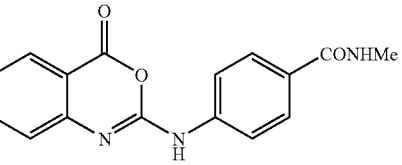 | 2-(4-N-Methylcarbamoylphenylamino)-4H-3,1-benzoxazin-4-one |
| 47 | 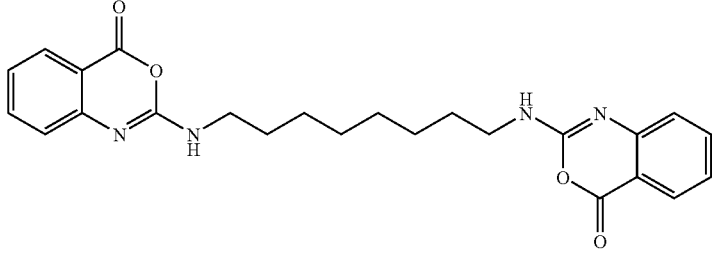 | 2,2'-(1,8-Octylidenediamino)-bis-4H-3,1-benzoxazin-4-one |

TABLE 1-continued

| Reference Number | Structure | Compound Name |
| --- | --- | --- |
| 48 | 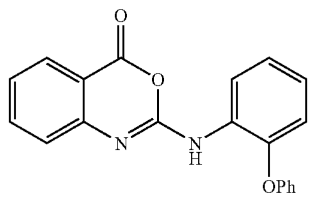 | 2-(2-Phenoxyphenylamino)-4H-3,1-benzoxazin-4-one |
| 49 | 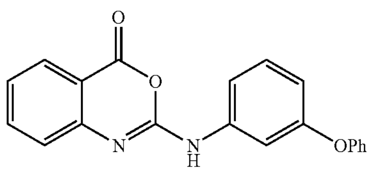 | 2-(3-phenoxyphenylamino)-4H-3,1-benzoxazin-4-one |
| 50 | 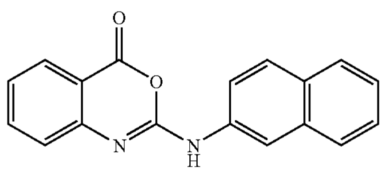 | 2-(Naphth-2-ylamino)-4H-3,1-benzoxazin-4-one |
| 51 | 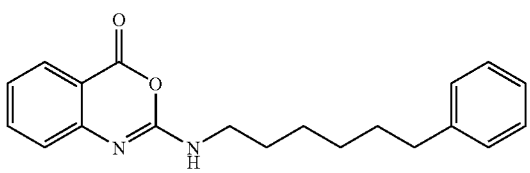 | 2-(6-Phenylhexylamino)-4H-3,1-benzoxazin-4-one |
| 52 | 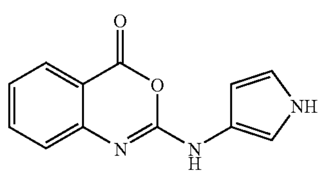 | 2-(Pyrrol-3-ylamino)-4H-3,1-benzoxazin-4-one |
| 53 | 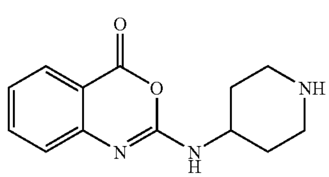 | 2-(Piperidin-4-ylamino)-4H-3,1-benzoxazin-4-one |
| 54 | 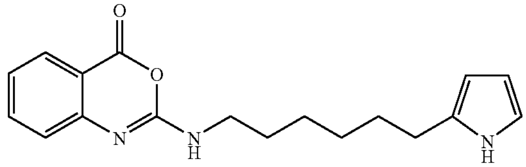 | 2-[6-(Pyrrol-2-yl)-hexylamino]-4H-3,1-benzoxazin-4-one |
| 55 | 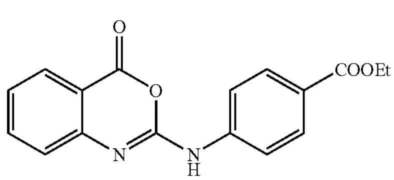 | 2-(4-Ethoxycarbonyl phenylamino)-4H-3,1-benzoxazin-4-one |

TABLE 1-continued

| Reference Number | Structure | Compound Name |
|---|---|---|
| 56 | 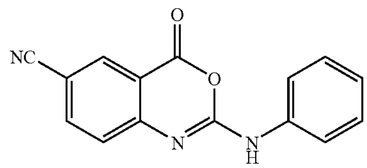 | 6-Cyano-2-phenylamino-4H-3,1-benzoxazin-4-one |
| 57 | 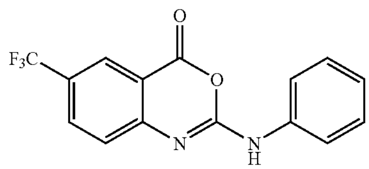 | 2-Phenyl-6-Trifluoromethyl-4H-3,1-benzoxazin-4-one |
| 58 | 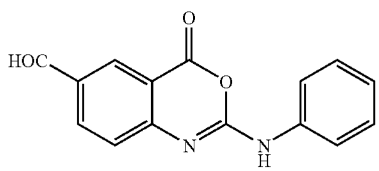 | 6-Formyl-2-phenylamino-4H-3,1-benzoxazin-4-one |
| 59 | 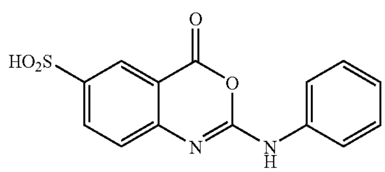 | 2-Phenylamino-4H-3,1-benzoxazin-4-one-6-sulfinic acid |
| 60 | 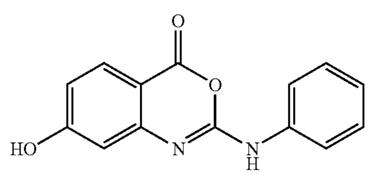 | 7-Hydroxy-2-phenylamino-4H-3,1-benzoxazin-4-one |
| 61 | 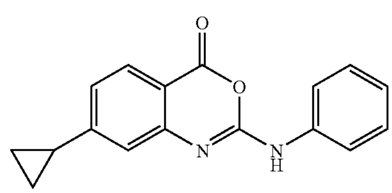 | 7-Cyclopropyl-2-phenylamino-4H-3,1-benzoxazin-4-one |
| 62 | 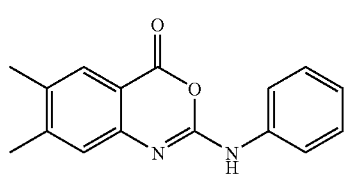 | 6,7-Dimethyl-2-phenylamino-4H-3,1-benzoxazin-4-one |
| 63 | 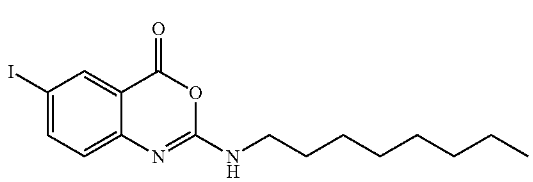 | 6-Iodo-2-octylamino-4H-3,1-benzoxazin-4-one |

TABLE 1-continued

| Reference Number | Structure | Compound Name |
|---|---|---|
| 64 | 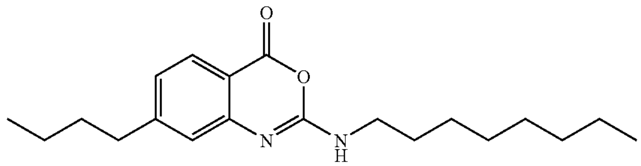 | 7-Butyl-2-octylamino-4H-3,1-benzoxazin-4-one |
| 65 | 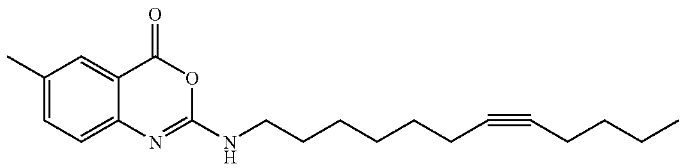 | 6-Methyl-2-(dodeca-7-ynylamino)-4H-3,1-benzoxazin-4-one |
| 66 | 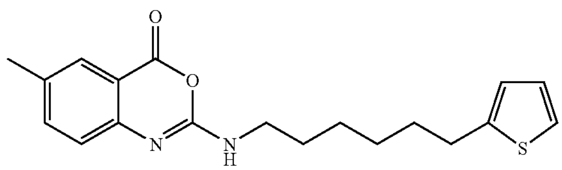 | 6-Methyl-2-[6-(thien-2-yl)hexylamino]-4H-3,1-benzoxazin-4-one |
| 67 | 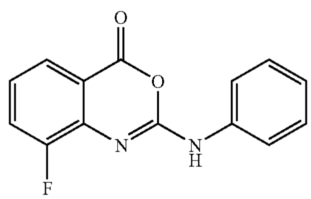 | 8-Fluoro-2-phenylamino-4H-3,1-benzoxazin-4-one |
| 68 | 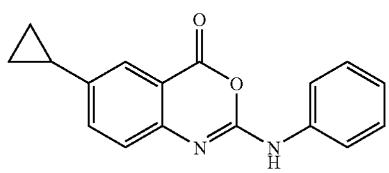 | 6-Cyclopropyl-2-phenylamino-4H-3,1-benzoxazin-4-one |
| 69 | 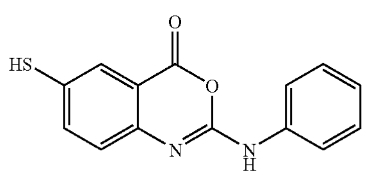 | 6-Mercapto-2-phenylamino-4H-3,1-benzoxazin-4-one |
| 70 | 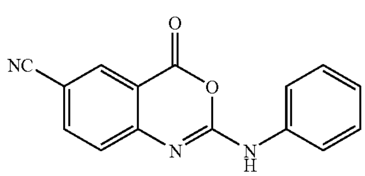 | 6-Cyano-2-phenylamino-4H-3,1-benzoxazin-4-one |

Compounds 2, 3, 5, 6, 8, 11-15 and 17-70 in Table 1 above are believed to be novel and as such represent preferred embodiments of the present invention.

Preferred compounds of formula (II) listed in Table 1 include compounds 1, 3, 5, 9, 17, 19, 20, 23 and 26.

Preferred compounds of formula (IIa) listed in Table 1 include compounds 11, 12, 14, 25, 29 and 30.

Preferred compounds of formula (IIb) listed in Table 1 include compounds 2, 6, 7, 8, 10, 15, 21, 24.

Particularly preferred compounds of formula (IIa) and (IIb) are:

2-(4-Phenoxyphenylamino)-4H-3,1-benzoxazin-4-one 2-(4-Butoxycarbonylphenylamino)-6-methyl-4H-3,1-benzoxazin-4-one 6-Methyl-2-(4-phenoxyphenylamino)-4H-3,1-benzoxazin-4-one 2-(4-Hexylphenylamino)-6-methyl-4H-3,1-benzoxazin-4-one 7-Methyl-2-(4-phenoxyphenylamino)-4H-3,1-benzoxazin-4-one 2-(4-Benzoylphenylamino)-7-methyl-4H-3,1-benzoxazin-4-one 2-(4-Phenoxyphenylamino)-7-trifluoromethyl-4H-3,1-benzoxazin-4-one Preferred compounds of the invention listed above extend to the tautomers thereof, as well as (but not limited to) pharmaceutically acceptable salts, esters, amides or prodrugs thereof or a derivative with one or more lipid groups (natural or synthetic) attached.

A third aspect of the invention provides a process for the manufacture of any one or more of the novel compounds or derivatives according to the first and/or second aspects of the invention. Thus, the present invention provides a process for the preparation of a novel compound of formula (II) in particular a compound of formula (IIa) which process comprises:

Process (A) cyclising a compound of formula (III)

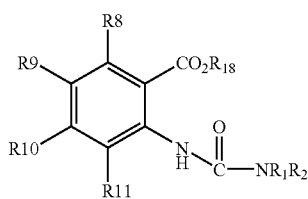

(III)

wherein $R^1$ and $R^8$-$R^{11}$ are as hereinbefore defined and $R^{18}$ is hydrogen or $C_{1-6}$alkyl, or:

Process (B) reacting a compound of formula (IV)

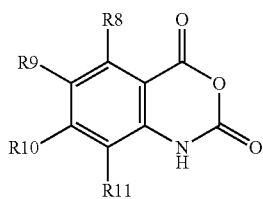

(IV)

with an amine of formula (V)

$R^1R^2NH$ (V)

or:

Process (C) converting a compound of formula (I), (II), (IIa) or (IIb) into a different compound of formula (IIa) or (IIb), by, for example,
  (i) reduction of a compound of formula (I), (II), (IIa) or (IIb) wherein any of $R^1$, $R^8$, $R^9$, $R^{10}$ and $R^{11}$ contains an alkenyl or alkynyl group or moiety, to the corresponding alkyl or alkenyl group or moiety; or
  (ii) alkylation of a compound of formula (I), (II), (IIa) or (IIb) where one or more of $R^8$, $R^9$, $R^{10}$ and $R^{11}$ represents a halogen atom.

Process (A) may be effected by reacting a compound (III) with a dehydrating agent in an organic solvent. Suitable dehydrating agents include sulphuric acid, and when $R^{18}$ is hydrogen, 1-(3-dimethylaminopropyl)-3-ethylcarbodiimide hydrochloride (EDC) or polymer supported EDC. The reaction may be effected at a temperature in the range 10 to 50° C., preferably ambient temperature e.g. 20-30° C. When polymer supported EDC is employed it may be removed by filtration at the end of the reaction, and the product isolated from solution by standard procedures, such as removal of the solvent and purification by flash column chromatography. Alternatively the cyclisation may be effected using concentrated sulphuric acid.

Alternatively, cyclisation according to process (A) may be effected by reaction with excess chloroformate or by addition of another cyclisation reagent, which promotes ring closure. Suitable cyclisation reagents include for example, methyl chloroformate, carbonyl diimidazole, acetic anhydride, phosgene, oxalyl chloride, thionyl chloride or a peptide coupling agent such as dicyclohexyl carbodiimide (DCC). The cyclisation reagent is preferably phosgene, triphosgene or thionyl chloride. When a chloroformate is employed this is preferably a low molecular weight chloroformate, on grounds of cost and ease of removing the resulting alcohol.

Compounds of the formula (III) may themselves be prepared according to a variety of methods. Thus for example a compound of formula:

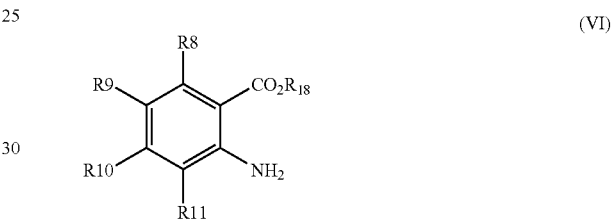

(VI)

can be reacted with an isocyanate of formula (VII):

$O=C=N-R^1$ (VII)

The reaction carried out in an inert organic solvent, such as an ether e.g. tetrahydrofuran, an aliphatic hydrocarbon such as pentane or hexane; a halogenated hydrocarbon such as dichloromethane; or an aromatic hydrocarbon such as benzene or toluene, and usually at ambient temperature. The intermediate urea may cyclise directly in a 'one pot' reaction, without isolation. Alternatively, if desired the urea may be isolated prior to cyclisation. Similarly any unreacted urea intermediate may be cyclised in a subsequent reaction step. It will be appreciated that the above reaction results in a compound (III) where $R^2$ is hydrogen.

Alternatively a compound of formula (III) may be prepared by reacting an isocyanate of formula (VIII):

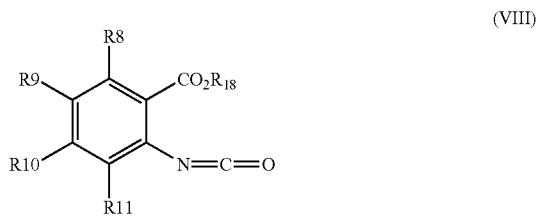

(VIII)

(wherein $R^8$, $R^9$, $R^{10}$, $R^{11}$ and $R^{18}$ are as hereinbefore defined)

with an amine of formula (V) $R^1R^2NH$.

Compounds of formula (III) may also be prepared from compounds of formula (IX)

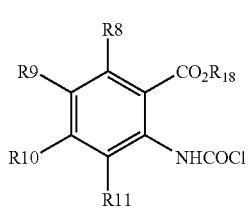
(IX)

by reaction with an amine $R^1R^2NH$.

Compounds (IX) may themselves be prepared by reacting a compound (VI) with an amine (V) in the presence of trichloromethyl chloroformate and in a solvent such as tetrahydrofuran or dimethyl formamide.

Process (B) may be effected by reacting a compound of formula (IV) with an amine $R^1R^2NH$ in the presence of a base e.g. sodium hydroxide, followed by cyclisation, for example as described for process (A).

Compounds of formula (IV) may be obtained by cyclisation of a compound of formula (VI) wherein $R^{18}$ is hydrogen using for example phosgene or a synthetic equivalent.

In process (C), reduction of an alkenyl or alkynyl group may be effected for example by catalytic hydrogenation using e.g. 10% palladium on charcoal in an alcoholic solvent, such as ethanol, under 1 atmosphere of hydrogen gas.

Alkylation according to process (C)(ii) may be effected using a Stille or other palladium catalysed cross-coupling process, using e.g. tetra-alkyl tin such as tetramethyl tin and $PhCH_2Pd(PPh_3)_2Cl$ in HMPA at elevated temperature e.g. 50-100° C. Other halides or pseudohalides e.g. triflates may be employed as starting materials.

Further methodology for preparing 2-amino-1,3-benzoxazin-4-one derivatives is described in *J. Med. Chem.* 1990, 33(2):464-479 and *J. Med. Chem.* 1998 41:1060-1067, as well as U.S. Pat. No. 4,657,893.

A fourth aspect of the invention is a compound according to the first and/or second aspects of the invention (i.e. compounds of formulae (I), (II) and (IIa)), for use in medicine. Preferred features of the first and second aspects of the invention also apply to the fourth aspect. Further details of the fourth aspect of the invention are set out in the text which follows.

A fifth aspect of the invention relates to a compound according to the first and/or second aspects of the invention for use in the inhibition of an enzyme whose preferred mode of action is to catalyse the hydrolysis of an ester functionality. This includes both in vivo and in vitro uses and other uses such as industrial uses. Such an enzyme is one which catalyses the breakdown of a substrate containing an ester functionality by the addition of water, resulting in the cleavage of a chemical bond. Such enzymes are involved in key processes in the body. Enzymes according to this invention include lipases (hydrolyse fatty acid esters), esterases (hydrolyse esters) and phosphatases (hydrolyse phosphate esters).

The enzyme is preferably a lipase. Lipases include pancreatic lipase, gastric lipase, lipoprotein lipase, lingual lipase, adipose tissue lipase, hormone sensitive lipase, phospholipase A1, A2, B, C, D etc., hepatic lipase, and other triacyl, diacyl and monoacylglycerol lipases in the mammalian body. Many similar such lipases are also known in plants, fungi and microorganisms.

Also covered are esterase enzymes and phosphatase enzymes. Esterase enzymes include pig liver esterase, cholesteryl esterase, retinyl esterase, 1-alkyl-2-glycerophosphocholine esterase, carboxylic ester hydrolases and cholesterol esterase. Phosphatase enzymes include serine/threonine phosphatases PP1, PP2 and PP3, phosphoprotein phosphatase, myosin-light-chain phosphatase, protein phosphatase 2C and protein tyrosine phosphatase.

Compounds according to the invention, for use in medicine, are primarily for use in relation to the prevention and/or treatment of a medical condition such as obesity, hyperlipaemia, hyperlipidaemia and related diseases such as hyperglycaemia (type II diabetes), hypertension, cardiovascular disease, stroke, gastrointestinal disease and gastrointestinal conditions. Compounds according to the first and/or second aspects of the invention are useful in these and other conditions due to their ability to inhibit an enzyme whose preferred mode of action is to catalyse the hydrolysis of an ester functionality. The invention also relates to non-medical weight loss, such as cosmetic weight loss and includes improving bodily appearance in general. Throughout this text, the prevention and/or treatment of any disorder means any effect which mitigates any damage or any medical disorder, to any extent, and includes prevention and treatment themselves. The term "treatment" means any amelioration of disorder, disease, syndrome, condition, pain or a combination of two or more thereof.

Clearly, an important application of the invention is in relation to weight loss (of all kinds as described above) in humans. However, the invention applies to medical and non-medical weight loss in any animal whose metabolism of fat and fat derivatives involves an enzyme whose preferred mode of action is to catalyse the hydrolysis of an ester functionality. Thus, the invention has veterinary application and is particularly useful in relation to medical and non-medical weight loss in companion animals such as pet cats and dogs as well as in animals which provide meat for human consumption. In the case of the latter, the application of the present invention is to reduce fat content in order to provide a leaner meat product.

It is also believed that the compounds may be useful in reducing levels of toxins (e.g. dioxins and PCBs) stored in body fat. Without wishing to be bound by theory, it is believed that increasing the amount of undigested fat passing through the body enhances diffusion of toxins from fat stored in the body into fats in the blood, and thence into the intestine.

The fifth aspect of the invention has important applications. It includes test and diagnostic methods and the control and inhibition of unwanted enzymes, preferably lipases, in any process or in any product. The processes or products which preferably involve a lipase include processing of agricultural commodities (e.g. oilseeds), recovery and isolation of enzymes from biotechnological processes (e.g. involving lysis of microorganisms), the manufacture and extraction of crude oil (especially oil and plastics), the industrial manufacture of triglycerides or other fats, manufacture of healthcare goods which comprise surfactants, soap or detergent (e.g. bath oils, creams), the manufacturing and processing of liposomes (e.g. healthcare products, diagnostics, gene therapy), the treatment of industrial waste (e.g. paper effluent treatment) and preventing the degradation of foodstuff which comprises a fat (e.g. chocolate processing). Thus, the invention also relates to these products and processes, e.g. a foodstuff which comprises a compound according to the first aspect of the invention, in particular foodstuffs which have a high fat content such as cakes, biscuits, pastry-products and the like and chocolate products. The preferred features of the fifth aspect of the invention, including the preferred enzymes are as discussed for the previous aspects of the invention.

A sixth aspect of the invention provides a composition comprising a novel compound according to the first and second aspects of the invention, in combination with a pharmaceutically acceptable carrier or diluent. Suitable carriers and/or diluents are well known in the art and include pharmaceutical grade starch, mannitol, lactose, magnesium stearate, sodium saccharin, talcum, cellulose, glucose, sucrose (or other sugar), magnesium carbonate, gelatin, oil, alcohol, detergents, emulsifiers or water (preferably sterile). The composition may be a mixed preparation of a composition or may be a combined preparation for simultaneous, separate or sequential use (including administration).

The compounds according to the invention for use in the aforementioned indications may be administered by any convenient method, for example by oral (including by inhalation), parenteral, mucosal (e.g. buccal, sublingual, nasal), rectal or transdermal administration and the compositions adapted accordingly.

For oral administration, the compounds can be formulated as liquids or solids, for example solutions, syrups, suspensions or emulsions, tablets, capsules and lozenges.

A liquid formulation will generally consist of a suspension or solution of the compound or physiologically acceptable salt in a suitable aqueous or non-aqueous liquid carrier(s) for example water, ethanol, glycerine, polyethylene glycol or an oil. The formulation may also contain a suspending agent, preservative, flavouring or colouring agent.

A composition in the form of a tablet can be prepared using any suitable pharmaceutical carrier(s) routinely used for preparing solid formulations. Examples of such carriers include magnesium stearate, starch, lactose, sucrose and microcrystalline cellulose.

A composition in the form of a capsule can be prepared using routine encapsulation procedures. For example, powders, granules or pellets containing the active ingredient can be prepared using standard carriers and then filled into a hard gelatin capsule; alternatively, a dispersion or suspension can be prepared using any suitable pharmaceutical carrier(s), for example aqueous gums, celluloses, silicates or oils and the dispersion or suspension then filled into a soft gelatin capsule.

Compositions for oral administration may be designed to protect the active ingredient against degradation as it passes through the alimentary tract, for example by an outer coating of the formulation on a tablet or capsule.

Typical parenteral compositions consist of a solution or suspension of the compound or physiologically acceptable salt in a sterile aqueous carrier or non-aqueous or parenterally acceptable oil, for example polyethylene glycol, polyvinyl pyrrolidone, lecithin, arachis oil or sesame oil. Alternatively, the solution can be lyophilised and then reconstituted with a suitable solvent just prior to administration.

Compositions for nasal or oral administration may conveniently be formulated as aerosols, drops, gels and powders. Aerosol formulations typically comprise a solution or fine suspension of the active substance in a physiologically acceptable aqueous or non-aqueous solvent and are usually presented in single or multidose quantities in sterile form in a sealed container, which can take the form of a cartridge or refill for use with an atomising device. Alternatively the sealed container may be a unitary dispensing device such as a single dose nasal inhaler or an aerosol dispenser fitted with a metering valve which is intended for disposal once the contents of the container have been exhausted. Where the dosage form comprises an aerosol dispenser, it will contain a pharmaceutically acceptable propellant. The aerosol dosage forms can also take the form of a pump-atomiser.

Compositions suitable for buccal or sublingual administration include tablets, lozenges and pastilles, wherein the active ingredient is formulated with a carrier such as sugar and acacia, tragacanth, or gelatin and glycerin.

Compositions for rectal or vaginal administration are conveniently in the form of suppositories (containing a conventional suppository base such as cocoa butter), pessaries, vaginal tabs, foams or enemas.

Compositions suitable for transdermal administration include ointments, gels and patches, and injections, including powder injections.

Conveniently the composition is in unit dose form such as a tablet, capsule or ampoule.

The compositions of the sixth aspect of the invention are useful in the prevention and/or treatment of obesity, obesity-related disorder, other medical weight loss and non-medical related weight loss. Preferred features of this aspect of the invention are as described above for the first to fifth aspects of the invention.

A seventh aspect of the invention provides a process for the manufacture of a composition according to the sixth aspect of the invention. The manufacture can be carried out by standard techniques well known in the art and involves combining a compound according to the first or second aspect of the invention and the pharmaceutically acceptable carrier or diluent. The composition may be in any form including a tablet, a liquid, a capsule, and a powder or in the form of a food product, e.g. a functional food. In the latter case the food product itself may act as the pharmaceutically acceptable carrier.

An eighth aspect of the invention provides a method for the prevention and/or treatment of obesity or an obesity-related disorder, the method comprising the administration of a compound according to the first or second aspect of the invention, preferably in combination with a pharmaceutically acceptable carrier or diluent (as per the sixth aspect of the invention). Obesity-related disorders include hyperlipeamia, hyperlipideamia, hyperglycaemia, hypertension, cardiovascular disease, stroke, gastrointestinal disease and gastrointestinal conditions. The compound or composition is preferably administered to a patient in need thereof and in a quantity sufficient to prevent and/or treat the symptoms of the condition, disorder or disease. For all aspects of the invention, particularly medical ones, the administration of a compound or composition has a dosage regime which will ultimately be determined by the attending physician and will take into consideration such factors such as the compound being used, animal type, age, weight, severity of symptoms, method of administration, adverse reactions and/or other contraindications. Specific defined dosage ranges can be determined by standard design clinical trials with patient progress and recovery being fully monitored. Such trials may use an escalating dose design using a low percentage of the maximum tolerated dose in animals as the starting dose in man.

The physiologically acceptable compounds of the invention will normally be administered in a daily dosage regimen (for an adult patient) of, for example, an oral dose of between 1 mg and 2000 mg, preferably between 30 mg and 1000 mg, e.g. between 10 and 250 mg or an intravenous, subcutaneous, or intramuscular dose of between 0.1 mg and 100 mg, preferably between 0.1 mg and 50 mg, e.g. between 1 and 25 mg of the compound of the formula (I) or a physiologically acceptable salt thereof calculated as the free base, the compound being administered 1 to 4 times per day. Suitably the compounds will be administered for a period of continuous therapy, for example for a week or more.

A ninth aspect of the invention provides a cosmetic method for maintaining a given weight, or for cosmetic weight loss, the method comprising the administration of a compound according to the first aspect of the invention, preferably in combination with a pharmaceutically acceptable carrier or diluent (as per the fifth aspect of the invention). The "medicament" is preferably administered to a patient in need thereof and in a quantity sufficient to maintain a given weight or for cosmetic weight loss.

The eighth and ninth aspects of the invention relate to methods of treatment of humans and other animals, in particular companion animals and other animals which provide meat for human consumption, such as cattle, pigs and sheep (all of any age).

The invention will now be described with reference to the following non-limiting examples.

Biological Test Methods and Results

Test Compounds

The benzoxazinone compounds used in the following tests are identified by the reference number assigned in Table 1 hereinbefore.

Measurement of Lipase Activity Using a Quinine Diimine Dye Colorimetric Assay

The inhibitory activity of the selected compounds to pancreatic lipase was measured in the following assay available from Sigma Ltd (Lipase PS™, catalog number 805-A):

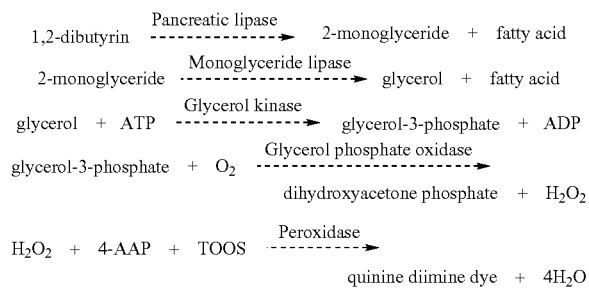

The glycerol released from the action of pancreatic and monoglyceride lipase was oxidised to release $H_2O_2$. The peroxidase reaction step then produces a quinine dye which is pink in colour and absorbs light at a wavelength of 550 nm.

Inhibitor

Individual compounds were dissolved in DMSO (dimethyl sulphoxide) at 10 mM. DMSO was used to avoid any problems with compounds being water-insoluble.

For individual compounds, the $IC_{50}$ (concentration at which lipase activity is inhibited to one half of the maximum) was calculated by measuring the inhibitory activity from log-dose response curves using a range of inhibitor concentrations.

Results

A range of compounds were assayed in the quinine diimine dye colorimetric assay which provides a rapid method to measure lipase inhibitory activity. None of the compounds tested interfered with the colorimetric reaction, i.e. they did not give false positive results.

A range of inhibitory activities for the tested benzoxazinone compounds were observed, indicating that these compounds are inhibitors of human pancreatic lipase. The following compounds had $IC_{50}$'s $\leq 1$ μM: 1-3, 5-12, 14, 15, 17, 19-21, 23-26, 28-30.

Measurement of lipase enzyme activity using a NaOH titration method

The inhibitory activity of the selected compounds to pancreatic lipase was measured in the assay described in Pasquier et al., 1986, Vol 7, Nutritional Biochemistry, 293-302.

Log dose/response curves were constructed using a range of inhibitor concentrations.

Results

Selected benzoxazinone compounds were tested in the NaOH titration assay. In this assay, the activity of porcine pancreatic lipase in a system containing lipid micelles is recorded. These conditions are therefore similar to those encountered in the gastrointestinal tract.

A range of inhibitory activities were observed for the tested benzoxazinone compounds in this assay indicating that these compounds are inhibitors of porcine pancreatic lipase. The following compounds had an $IC_{50} \leq 2$ μM: 1-3, 5, 8, 11, 12, 14-20, 24, 26, 28, 29, 30.

Thus, the results demonstrate that the tested benzoxazinones are inhibitors of fat digestion and that these compounds may be particularly suitable for the treatment of obesity.

Mouse Model Assay

Compound 24 was assayed in a mouse model as described by Isler et al., *British Journal of Nutrition*, 1995, 73:851-862 and was found to be a potent lipase inhibitor.

Synthesis of Intermediates

Synthesis of 4-substituted Anthranilic Acids

Example 4-octyl anthranilic acid (4-octyl-2-aminobenzoic acid)

Method based on that of L. A. Paquette et al. J. Am. Chem. Soc. 99, 3734 (1981)

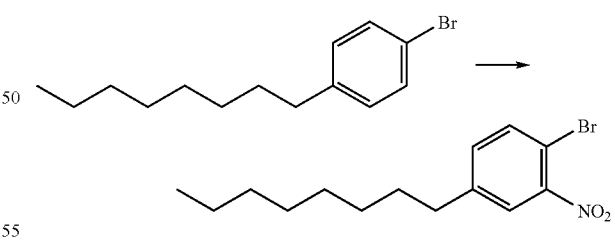

A solution of 1-bromo-4-octylbenzene (9.9 g, 36 mmol) in sulfuric acid (20 ml) was cooled in an ice bath. To this was added nitric acid (1.44 ml, 36 mmol). The ice bath was removed and the mixture stirred at room temperature for 20 minutes. A further portion of nitric acid was added (0.07 ml, 1.75 mmol), stirring being continued for a further 20 min. The mixture was poured into aqueous potassium carbonate, which was extracted with ethyl acetate. The organic extract was washed with saturated aqueous potassium carbonate, water and brine then dried ($MgSO_4$) and concentrated. Purification of the crude product by flash chromatography (1% EtOAc/ hexane) removed the unwanted (major) regioisomer and afforded the desired material as a yellow oil (1.7 g, 5.4 mmol).

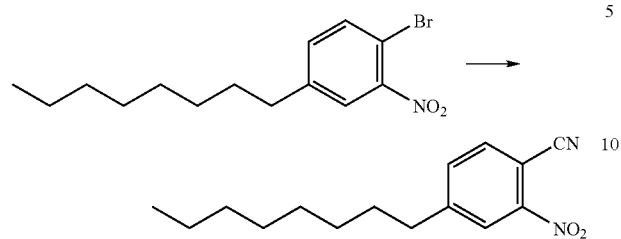

The substrate (1.7 g, 5.4 mmol), copper (I) cyanide (0.533 g, 5.9 mmol) and pyridine (20 ml) were refluxed at 150° C. for 2 days. Concentration in vacuo and purification by flash chromatography (10% to 20% EtOAc/hexane) gave the desired material as a brown oil (739 mg, 2.8 mmol)

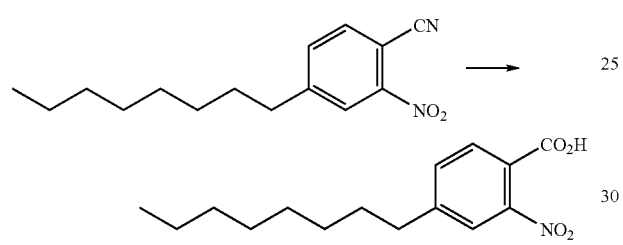

The substrate (694 mg, 2.7 mmol) was heated at 150° C. in a mixture of water (2 ml), AcOH (1 ml) and sulfuric acid (1 ml) for 2 days. The mixture was extracted with ethyl acetate, the organic phase being washed with water (×2), dried ($Na_2SO_4$) and concentrated to give the desired material (744 mg, 2.7 mmol).

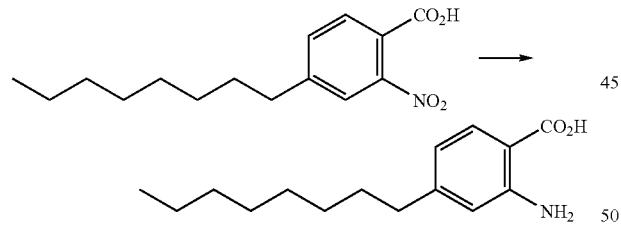

The starting material (744 mg, 2.7 mmol) was dissolved in ethanol (10 ml) and to this was added a slurry of 10% palladium on charcoal (40 mg) in ethanol (4 ml). The flask was flushed with nitrogen then hydrogen (1 atm) after which stirring was maintained overnight. Further portions of catalyst (5 mg and 25 mg) were added, the reaction being complete after a further 24 h. The reaction mixture was filtered through celite, thoroughly rinsing with methanol and ethyl acetate. Concentration gave the anthranilic acid (597 mg, 2.4 mmol) of sufficient purity for use without further purification; $\delta_H$ (400 MHz, $CDCl_3$) 0.79-0.81 (3H, m, Me), 1.12-1.36 (10H, m, 5×$CH_2$), 1.52 (2H, br.s, $ArCH_2CH_2$), 2.45 (2H, br.s, $ArCH_2$), 6.42 (2H, br.s, 2×ArH), 7.74 (1H, br.s, ArH); m/z ($ES^+$) 250 ($MH^+$).

Synthesis of Substituted Phenyl Isocyanates

Example 5

Preparation of 4-octylphenyl isocyanate

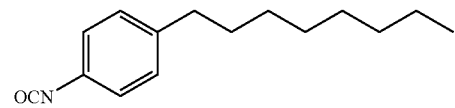

A solution of 4-octylaniline (0.3 ml, 1.3 mmol) and diisopropylamine (0.205 ml, 5.2 mmol) in THF (5 ml) was cooled to −10° C. A 20% solution of phosgene in toluene (1.3 ml, 2.6 mmol) was added, then the mixture was allowed to warm to r.t. and maintained at that temperature for 3 h. Excess phosgene was removed under a stream of nitrogen (scrubbed on exit with $NaOH_{(aq)}$) to give a solution of the crude isocyanate, which was used directly in the next step.

4-Benzoylphenylisocyanate was prepared by an analogous procedure from the corresponding aniline.

Substituted 4-phenoxyphenyl isocyanates can be prepared from the corresponding amines by known procedures.

SYNTHESIS OF COMPOUNDS ACCORDING TO THE INVENTION

Example 1

Synthesis of 2-(4-Butoxycarbonylphenylamino)-6-methyl-4H-3,1-benzoxazin-4-one (Reference number 14)

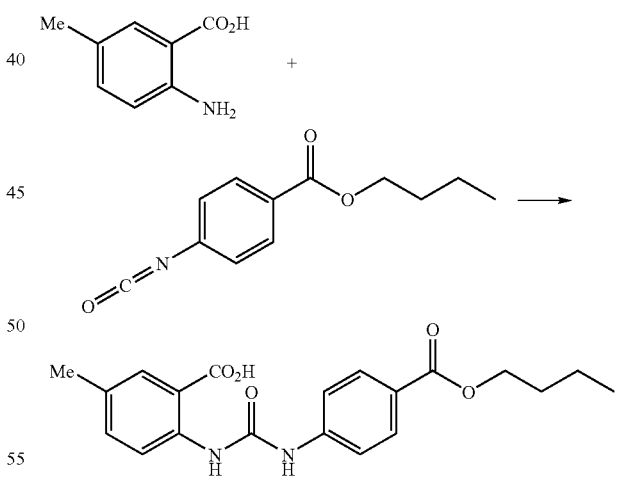

A solution of 2-amino-5-methylbenzoic acid (690 mg, 4.57 mmol) in THF (2 ml) was treated with 4-n-butoxycarbonylphenyl isocyanate (1.0 g, 4.57 mmol). The mixture was kept at room temperature for 24 h, during which time the solvent was allowed to evaporate to leave a pale brown solid (1.7 g, quant.); $\delta_H$ (400 MHz, DMSO-$d_6$) 0.93 (3H, t, J 7, $CH_2CH_3$), 1.41 (2H, tq, J, J' 7, $CH_2CH_3$), 1.67 (2H, tt, J, J' 7, $CH_2CH_2CH_3$), 2.28 (3H, s, $CH_3$), 4.23 (2H, t, J 7, $OCH_2$), 7.37 (1H, d, J 8, Ph), 7.77 (1H, s, Ph), 7.85-7.92 (4H, m, Ph), 8.24 (1H, d, J 8, Ph).

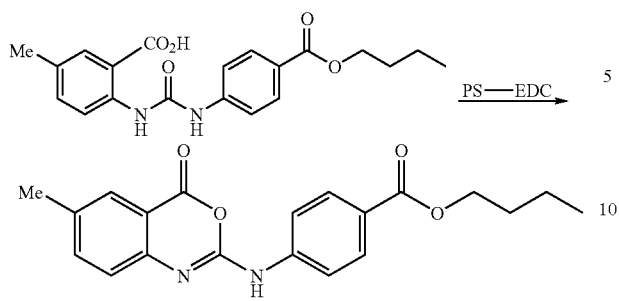

To a solution of the urea (185 mg, 0.5 mmol) in DMF (10 ml) was added polymer-supported EDC (PS-EDC) (0.8 mmol g$^{-1}$, 1.0 g). The resulting mixture was agitated at room temperature for 18 h, after which the resin was filtered off and washed with DMF (2×5 ml). The filtrate and washings were combined and evaporated under reduced pressure to afford the required compound as an off-white solid (150 mg, 85%); $\delta_H$ (400 MHz, DMSO-d$_6$) 0.94 (3H, t, J 7, CH$_2$CH$_3$), 1.42 (2H, tq, J, J' 7, CH$_2$CH$_3$), 1.69 (2H, tt, J, J' 7, CH$_2$CH$_2$CH$_3$), 2.39 (3H, s, CH$_3$), 4.25 (2H, t, J 7, OCH$_2$), 7.36 (1H, d, J 8, Ph), 7.63 (1H, d, J 8, Ph), 7.80 (1H, s, Ph),), 7.90-7.95 (4H, m, Ph); m/z (ES$^-$) 351 (M-H$^+$).

Example 2

Synthesis of 6-Methyl-2-(4-phenoxyphenylamino)-4H-3,1-benzoxazin-4-one (Reference number 15)

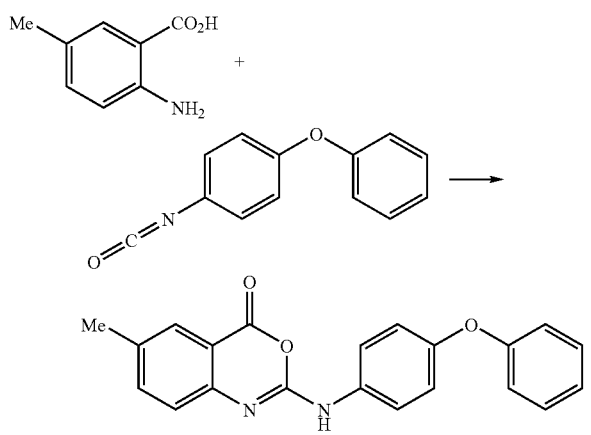

A solution of 2-amino-5-methylbenzoic acid (172 mg, 1.10 mmol) in THF (1 ml) was treated with 4-phenoxyphenyl isocyanate (241 mg, 1.10 mmol). The mixture was kept at room temperature for 24 h, during which time the solvent was allowed to evaporate to leave a pale brown solid. This was dissolved in DMF (5 ml) and added to a suspension of PS-EDC (0.8 mmol g$^{-1}$, 2.8 g) in DMF (20 ml). The resulting mixture was agitated at room temperature for 18 h, after which the resin was filtered off and washed with DMF (2×5 ml). The filtrate and washings were combined and evaporated under reduced pressure. Flash column chromatography over silica (20% ethyl acetate in hexane as eluent) afforded the required compound as an off-white solid (153 mg, 40%); $\delta_H$ (400 MHz, DMSO-d$_6$) 2.36 (3H, s, CH$_3$), 6.96 (2H, d, J 8, Ph), 7.04 (1H, d, J 8, Ph), 7.09 (1H, t, J 8, Ph), 7.26 (1H, d, J 8, Ph), 7.34-7.38 (2H, m, Ph), 7.55-7.56 (1H, m, Ph), 7.76-7.78 (4H, m, Ph); m/z (ES$^+$) 345 (MH$^+$).

Example 3

2-(3-chlorophenylamino)-6-octyl-4H-3,1-benzoxazin-4-one

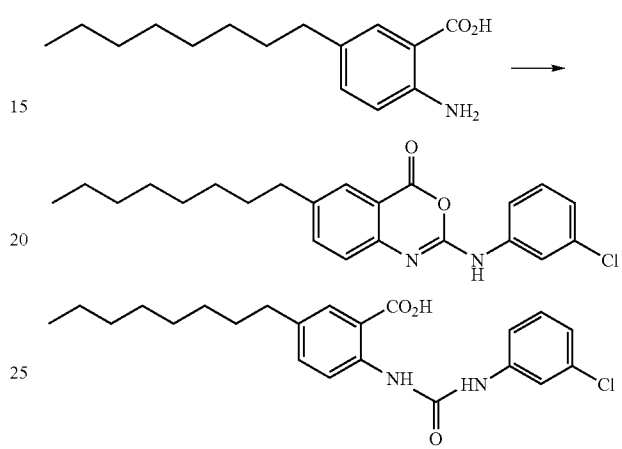

The anthranilic acid (200 mg, 0.8 mmol) was dissolved in anhydrous THF (1 ml), and to this was added 3-chlorophenylisocyanate (117 µl, 0.96 mmol). The mixture was stirred for 3 h before being concentrated. The residue was partitioned between water and ethyl acetate. The organic layer was washed with 5% aqueous citric acid, saturated aqueous sodium bicarbonate and brine then dried (MgSO$_4$) and concentrated to give an orange solid. This was purified by flash chromatography on silica (15% EtOAc/hexane to 100% EtOAc, then 10% EtOH/EtOAc) which gave, in order of elution, the benzoxazinone (18 mg, 0.05 mmol); $\delta_H$ (400 MHz, CDCl$_3$) 0.77-0.82 (3H, m, Me), 1.19-1.24 (10H, m, 5×CH$_2$), 1.55-1.57 (2H, m, ArCH$_2$CH$_2$), 2.56-2.62 (2H, m, ArCH$_2$), 7.00-7.32 (4H, m, 3×ArH, NH), 7.40-7.49 (2H, m, 2×ArH), 7.81-7.83 (2H, m, ArH); m/z (ES$^+$) 385 (MH$^+$) and the urea (160 mg, 0.4 mmol); m/z (ES$^-$) 401 (M-H)$^-$.

The residual urea may be cyclised in a separate step (as in the procedure below) to afford more benzoxazinone if required.

Example 4

7-Octyl-2-phenylamino-4H-3,1-benzoxazin-4-one (compound 23)

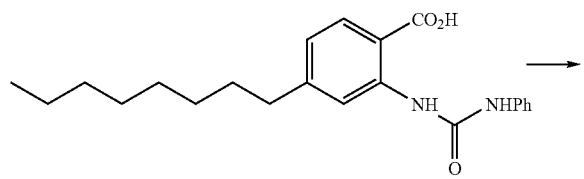

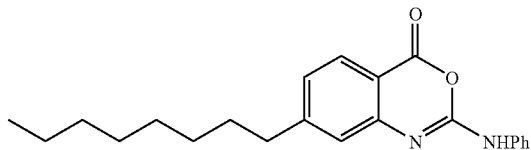

The urea (126 mg, 0.34 mmol) was suspended in dry DCM (4 ml). 1-[3-(Dimethylamino)propyl]-3-ethylcarbodiimide hydrochloride (EDC, 131 mg, 0.68 mmol) was added and the mixture stirred for 24 h. A further portion of EDC (131 mg, 0.68 mmol) was added and the mixture was stirred for a further 24 h. The mixture was diluted with ethyl acetate and washed with water, saturated aqueous sodium bicarbonate and brine, then dried ($Na_2SO_4$) and concentrated. This gave the desired benzoxazinone (89 mg, 0.25 mmol), which did not require further purification: $\delta_H$ (400 MHz, $CDCl_3$) 0.92 (3H, t, J 6.7, Me), 1.30-1.36 (10H, m, 5×$CH_2$), 1.68-1.70 (2H, m, $ArCH_2CH_2$), 2.71-2.75 (2H, m, $ArCH_2$), 6.80 (1H, br.s, NH), 7.13-7.21 (2H, m, 2×ArH), 7.28 (1H, s, ArH), 7.42-7.46 (2H, m, ArH), 7.70 (2H, d, J 8.2, ArH), 8.04 (1H, d, J 8.1, ArH); m/z ($ES^+$) 351 ($MH^+$).

Example 5

7-Methyl-2-(4-phenoxyphenyl)-4H-3,1-benzoxazin-4-one

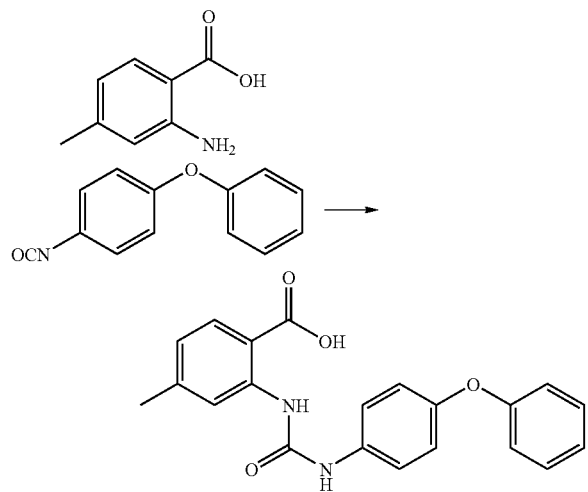

2-Amino-4-methylbenzoic acid (207 mg, 1.37 mmol) in THF (3 ml) was treated with 4-phenoxyphenyl isocyanate (289 mg, 1.37 mmol). The mixture was kept at r.t. for 48 h then diluted with ethyl acetate and washed with 2N HCl, water, saturated aqueous sodium bicarbonate and brine, dried ($Na_2SO_4$) and concentrated. The residue was chromatographed on silica (50% to 100% ethyl acetate/hexane gradient, then 1% methanol/ethyl acetate) to give a white solid (217 mg, 0.6 mmol, 44%); $\delta_H$ (400 MHz, DMSO-$d_6$) 2.28 (3H, s, Me), 6.72 (1H, d, J 8.0, ArH), 6.95 (4H, m, ArH), 7.08 (1H, t, J 6.9, ArH), 7.36 (2H, t, J 7.9, ArH), 7.56 (2H, d, J 8.7, ArH), 7.87 (1H, d, J 7.6, ArH), 8.11 (1H, s, ArH), 9.49 (1H, s, NH); m/z ($ES^-$) 362 (M-H)$^-$.

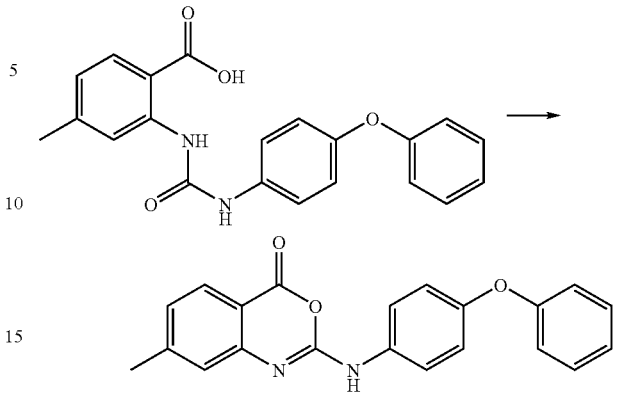

The urea (217 mg, 0.6 mmol) in DCM (4 ml) was treated with EDC (126 mg, 0.66 mmol). After 24 h and 48 h, further portions of EDC were added (115 mg each, 0.6 mmol). The mixture was diluted with ethyl acetate and washed with water, saturated aqueous sodium bicarbonate and brine then dried ($Na_2SO_4$) and concentrated to afford the benzoxazinone (137 mg, 0.4 mmol, 67%); $\delta_H$ (400 MHz, $CDCl_3$) 2.37 (3H, s, Me), 6.7 (1H, br.s, NH), 6.94-7.05 (6H, m, ArH), 7.14 (1H, s, ArH), 7.27 (2H, t, J 7.7, ArH), 7.54 (2H, d, J 8.7, ArH), 7.89 (1H, d, J 8.1, ArH); m/z ($ES^+$) 345 ($MH^+$).

The other compounds listed in Table 1 may be prepared in a similar manner to Examples 1 to 5 above. In particular the following compounds were prepared using the starting materials indicated:

| Compound number | Starting material 1 | Starting material 2 |
|---|---|---|
| 2 | 2-aminobenzoic acid | 4-butylphenyl isocyanate |
| 8 | 2-aminobenzoic acid | 4-phenoxyphenyl isocyanate |
| 10 | 2-aminobenzoic acid | 4(1-methylethyl)phenyl isocyanate |
| 11 | 2-aminobenzoic acid | 4-trifluoromethylphenyl isocyanate |
| 12 | 2-aminobenzoic acid | 3-trifluoromethylphenyl isocyanate |
| 13 | 2-amino-5-methylbenzoic acid | 1-naphthyl isocyanate |
| 14 | 2-amino-5-methylbenzoic acid | 4-butoxycarbonylphenyl isocyanate |
| 15 | 2-amino-5-methylbenzoic acid | 4-phenoxyphenyl isocyanate |
| 17 | 2-amino-4-fluorobenzoic acid | Phenyl isocyanate |
| 18 | 2-amino-6-fluorobenzoic acid | Phenyl isocyanate |
| 19 | 2-amino-4-methylbenzoic acid | Phenyl isocyanate |
| 20 | 2-amino-4-ethylbenzoic acid | phenyl isocyanate |
| 21 | 2-amino-5-methylbenzoic acid | 4-hexyl phenyl isocyanate |
| 22 | 2-amino-5-methylbenzoic acid | 4-heptyloxyphenyl isocyanate |
| 23 | 2-amino-4-octylbenzoic acid | Phenyl isocyanate |
| 24 | 2-amino-4-methylbenzoic acid | 4-phenoxyphenyl isocyanate |
| 25 | 2-amino-5-methylbenzoic acid | Hexadecylisocyanate |
| 26 | 2-amino-4-butylbenzoic acid | phenyl isocyanate |
| 27 | 2-amino-4-methylbenzoic acid | 2-phenoxyphenylisocyanate |
| 28 | 2-amino-4-methylbenzoic acid | 3-phenoxyphenylisocyanate |
| 29 | 2-amino-4-methylbenzoic acid | 4-benzoylphenyl isocyanate |
| 30 | 2-amino-4-trifluoromethyl benzoic acid | 4-phenoxyphenyl isocyanate |
| 31 | 2-amino-4-methylbenzoic acid | 4-octyl phenyl isocyanate |
| 32 | 3-aminopyridine-4-carboxylic acid | Phenyl isocyanate |
| 33 | 2-amino-4-methylbenzoic acid | cyanophenyl isocyanate |

The foregoing description details the specific compounds, composition, methods and uses which can be employed to practice the present invention. However, those skilled in the art will know how to use alternative reliable methods for aiming at alternative embodiments of the invention which are herein encompassed.

The invention claimed is:

1. A method for the treatment of obesity or an obesity-related disorder selected from the group consisting of hyperlipaemia, hyperlipidaemia, hyperglycaemia (type II diabetes), hypertension, cardiovascular disease, stroke, gastrointestinal disease, and gastrointestinal conditions, the method comprising administering to a subject in need thereof a therapeutically effective amount of a compound of formula (II):

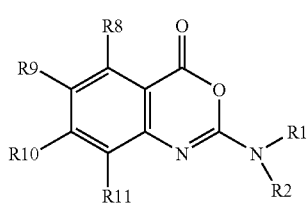

or a pharmaceutically acceptable salt, ester, amide or prodrug thereof,
wherein:
$R^1$ is a branched or unbranched alkyl or phenyl wherein said phenyl group can be substituted with one or more substituents independently chosen from the group consisting of halogen, alkyl, halosubstituted alkyl, —$CO_2R^4$, and —$OR^6$;
$R^2$ is hydrogen;
and where:
$R^4$ is alkyl;
$R^6$ is alkyl or phenyl;
and
$R^8$, $R^9$, $R^{10}$, and $R^{11}$ are each independently hydrogen, halo, alkyl, or haloalkyl.

2. The method of claim 1 wherein in the compound of formula (II)
$R^1$ is phenyl optionally substituted with —$OR^6$, where $R^6$ is phenyl;
$R^2$ is hydrogen;
$R^8$ is hydrogen or fluorine;
$R^9$ is lower branched or unbranched alkyl having 1 to 10 carbon atoms, haloalkyl, or a halogen;
$R^{10}$ is lower branched or unbranched alkyl having 1 to 10 carbon atoms, haloalkyl, or a halogen; and
$R^{11}$ is hydrogen, lower branched or unbranched alkyl having 1 to 10 carbon atoms, or halogen.

3. The method of claim 1 wherein in the compound of formula (II) $R^1$ represents phenyl substituted by a group selected from $OR^6$, $CO_2R^4$, $C_{1-10}$alkyl, or halo$C_{1-10}$alkyl, wherein $R^6$ is $C_{1-10}$alkyl or phenyl, and wherein $R^4$ is $C_{1-10}$alkyl.

4. The method of claim 1 wherein in the compound of formula (II) $R^1$ represents phenyl substituted by $OR^6$ wherein $R^6$ is phenyl.

5. The method of claim 2 wherein in the compound of formula (II) $R^1$ represents phenyl substituted by $OR^6$ wherein $R^6$ is phenyl.

6. The method of claim 1, wherein the step of administering the compound to a subject comprises administering the compound to a human.

7. The method of claim 1, wherein the step of administering the compound to a subject comprises administering the compound to an animal.

8. The method of claim 1, wherein the method is for the treatment of obesity.

9. The method of claim 1, wherein the method is for the treatment of an obesity-related disorder is selected from the group consisting of hyperlipaemia, hyperlipidaemia, hyperglycaemia (type II diabetes), hypertension, cardiovascular disease, stroke, gastrointestinal disease, and gastrointestinal conditions.

10. A method for the treatment of obesity or an obesity-related disorder selected from the group consisting of hyperlipaemia, hyperlipidaemia, hyperglycaemia (type II diabetes), hypertension, cardiovascular disease, stroke, gastrointestinal disease and gastrointestinal conditions, the method comprising administering to a subject in need thereof a therapeutically effective amount of a compound selected from:
2-phenylamino-4H-3,1-benzoxazin-4-one;
2-(4-butylphenylamino)-4H-3,1-benzoxazin-4-one;
6-chloro-2-phenylamino-4H-3,1-benzoxazin-4-one;
2-butylamino-4H-3,1-benzoxazin-4-one;
6-methyl-2-phenylamino-4H-3,1-benzoxazin-4-one;
2-(4-methoxyphenylamino)-4H-3,1-benzoxazin-4-one;
2-(4-methylphenylamino)-4H-3,1-benzoxazin-4-one;
2-(4-phenoxyphenylamino)-4H-3,1-benzoxazin-4-one;
2-(4-chlorophenylamino)-4H-3,1-benzoxazin-4-one;
2-[4(1-methylethyl)phenylamino]-4H-3,1-benzoxazin-4-one;
2-(4-trifluoromethylphenylamino)-4H-3,1-benzoxazin-4-one;
2-(3-trifluoromethylphenylamino)-4H-3,1-benzoxazin-4-one;
2-(4-butoxycarbonylphenylamino)-6-methyl-4H-3,1-benzoxazin-4-one;
6-methyl-2-(4-phenoxyphenylamino)-4H-3,1-benzoxazin-4-one;
2-ethylamino-4H-3,1-benzoxazin-4-one;
7-fluoro-2-phenylamino-4H-3,1-benzoxazin-4-one;
5-fluoro-2-phenylamino-4H-3,1-benzoxazin-4-one;
7-methyl-2-phenylamino-4H-3,1-benzoxazin-4-one;
7-ethyl-2-Phenylamino-4H-3,1-benzoxazin-4-one;
2-(4-hexylphenylamino)-6-methyl-4H-3,1-benzoxazin-4-one;
2-(4-heptyloxyphenylamino)-6-methyl-4H-3,1-benzoxazin-4-one;
7-octyl-2-phenylamino-4H-3,1-benzoxazin-4-one;
7-methyl-2-(4-phenoxyphenylamino)-4H-3,1-benzoxazin-4-one;
2-hexadecylamino-6-methyl-4H-3,1-benzoxazin-4-one;
7-butyl-2-phenylamino-4H-3,1-benzoxazin-4-one;
7-methyl-2-(2-phenoxyphenylamino)-4H-3,1-benzoxazin-4-one;
7-methyl-2-(3-phenoxyphenylamino)-4H-3,1-benzoxazin-4-one;
2-(4-benzoylphenylamino)-7-methyl-4H-3,1-benzoxazin-4-one;
2-(4-phenoxyphenylamino)-7-trifluoromethyl-4H-3,1-benzoxazin-4-one;
or a pharmaceutically acceptable salt, ester, or amide thereof.

11. The method of claim 10, wherein the compound is selected from:
- 2-phenylamino-4H-3,1-benzoxazin-4-one;
- 6-chloro-2-phenylamino-4H-3,1-benzoxazin-4-one;
- 6-methyl-2-phenylamino-4H-3,1-benzoxazin-4-one;
- 2-(4-chlorophenylamino)-4H-3,1-benzoxazin-4-one;
- 7-fluoro-2-phenylamino-4H-3,1-benzoxazin-4-one;
- 7-methyl-2-phenylamino-4H-3,1-benzoxazin-4-one;
- 7-ethyl-2-Phenylamino-4H-3,1-benzoxazin-4-one;
- 7-octyl-2-phenylamino-4H-3,1-benzoxazin-4-one;
- 7-butyl-2-phenylamino-4H-3,1-benzoxazin-4-one;
- or a pharmaceutically acceptable salt, ester, or amide thereof.

12. The method of claim 10, wherein the compound is selected from:
- 2-(4-trifluoromethylphenylamino)-4H-3,1-benzoxazin-4-one;
- 2-(3-trifluoromethylphenylamino)-4H-3,1-benzoxazin-4-one;
- 2-(4-butoxycarbonylphenylamino)-6-methyl-4H-3,1-benzoxazin-4-one;
- 2-hexadecylamino-6-methyl-4H-3,1-benzoxazin-4-one;
- 2-(4-benzoylphenylamino)-7-methyl-4H-3,1-benzoxazin-4-one;
- 2-(4-phenoxyphenylamino)-7-trifluoromethyl-4H-3,1-benzoxazin-4-one;
- or a pharmaceutically acceptable salt, ester, or amide thereof.

13. The method of claim 10, wherein the compound is selected from:
- 2-(4-butylphenylamino)-4H-3,1-benzoxazin-4-one;
- 2-(4-methoxyphenylamino)-4H-3,1-benzoxazin-4-one;
- 2-(4-methylphenylamino)-4H-3,1-benzoxazin-4-one;
- 2-(4-phenoxyphenylamino)-4H-3,1-benzoxazin-4-one;
- 2-[4(1-methylethyl)phenylamino]-4H-3,1-benzoxazin-4-one;
- 6-methyl-2-(4-phenoxyphenylamino)-4H-3,1-benzoxazin-4-one;
- 2-(4-hexylphenylamino)-6-methyl-4H-3,1-benzoxazin-4-one;
- 7-methyl-2-(4-phenoxyphenylamino)-4H-3,1-benzoxazin-4-one;
- or a pharmaceutically acceptable salt, ester, or amide thereof.

14. The method of claim 10, wherein the compound is 2-(4-phenoxyphenylamino)-4H-3,1-benzoxazin-4-one.

15. The method of claim 10, wherein the compound is 2-(4-butoxycarbonylphenylamino)-6-methyl-4H-3,1-benzoxazin-4-one.

16. The method of claim 10, wherein the compound is 6-methyl-2-(4-phenoxyphenylamino)-4H-3,1-benzoxazin-4-one.

17. The method of claim 10, wherein the compound is 2-(4-hexylphenylamino)-6-methyl-4H-3,1-benzoxazin-4-one.

18. The method of claim 10, wherein the compound is 7-methyl-2-(4-phenoxyphenylamino)-4H-3,1-benzoxazin-4-one.

19. The method of claim 10, wherein the compound is 2-(4-benzoylphenylamino)-7-methyl-4H-3,1-benzoxazin-4-one.

20. The method of claim 10, wherein the compound is 2-(4-phenoxyphenylamino)-7-trifluoromethyl-4H-3,1-benzoxazin-4-one.

21. The method of claim 10, wherein the method is for the treatment of obesity.

22. The method of claim 14, wherein the method is for the treatment of obesity.

23. The method of claim 15, wherein the method is for the treatment of obesity.

24. The method of claim 16, wherein the method is for the treatment of obesity.

25. The method of claim 17, wherein the method is for the treatment of obesity.

26. The method of claim 18, wherein the method is for the treatment of obesity.

27. The method of claim 19, wherein the method is for the treatment of obesity.

28. The method of claim 20, wherein the method is for the treatment of obesity.

29. The method of claim 10, wherein the method is for the treatment of an obesity-related disorder is selected from the group consisting of hyperlipaemia, hyperlipidaemia, hyperglycaemia (type II diabetes), hypertension, cardiovascular disease, stroke, gastrointestinal disease, and gastrointestinal conditions.

30. The method of claim 14, wherein the method is for the treatment of an obesity-related disorder is selected from the group consisting of hyperlipaemia, hyperlipidaemia, hyperglycaemia (type II diabetes), hypertension, cardiovascular disease, stroke, gastrointestinal disease, and gastrointestinal conditions.

31. The method of claim 15, wherein the method is for the treatment of an obesity-related disorder is selected from the group consisting of hyperlipaemia, hyperlipidaemia, hyperglycaemia (type II diabetes), hypertension, cardiovascular disease, stroke, gastrointestinal disease, and gastrointestinal conditions.

32. The method of claim 16, wherein the method is for the treatment of an obesity-related disorder is selected from the group consisting of hyperlipaemia, hyperlipidaemia, hyperglycaemia (type II diabetes), hypertension, cardiovascular disease, stroke, gastrointestinal disease, and gastrointestinal conditions.

33. The method of claim 17, wherein the method is for the treatment of an obesity-related disorder is selected from the group consisting of hyperlipaemia, hyperlipidaemia, hyperglycaemia (type II diabetes), hypertension, cardiovascular disease, stroke, gastrointestinal disease, and gastrointestinal conditions.

34. The method of claim 18, wherein the method is for the treatment of an obesity-related disorder is selected from the group consisting of hyperlipaemia, hyperlipidaemia, hyperglycaemia (type II diabetes), hypertension, cardiovascular disease, stroke, gastrointestinal disease, and gastrointestinal conditions.

35. The method of claim 19, wherein the method is for the treatment of an obesity-related disorder is selected from the group consisting of hyperlipaemia, hyperlipidaemia, hyperglycaemia (type II diabetes), hypertension, cardiovascular disease, stroke, gastrointestinal disease, and gastrointestinal conditions.

36. The method of claim 20, wherein the method is for the treatment of an obesity-related disorder is selected from the group consisting of hyperlipaemia, hyperlipidaemia, hyperglycaemia (type II diabetes), hypertension, cardiovascular disease, stroke, gastrointestinal disease, and gastrointestinal conditions.

* * * * *